(12) United States Patent
Washizu et al.

(10) Patent No.: US 7,076,127 B2
(45) Date of Patent: Jul. 11, 2006

(54) OPTICAL SWITCH AND SAFETY APPARATUS USING THE SAME

(75) Inventors: Shintaro Washizu, Shizuoka (JP); Yuki Matsunami, Shizuoka (JP); Takatoshi Kinoshita, Aichi (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 83 days.

(21) Appl. No.: 10/752,024

(22) Filed: Jan. 7, 2004

(65) Prior Publication Data
US 2004/0136643 A1    Jul. 15, 2004

(30) Foreign Application Priority Data
Jan. 14, 2003   (JP)   ............... 2003-005973
Jan. 14, 2003   (JP)   ............... 2003-005974

(51) Int. Cl.
G02B 6/42   (2006.01)
(52) U.S. Cl. ............. 385/16; 385/19; 250/227.27; 327/6
(58) Field of Classification Search ............. 385/16–24; 250/227.14, 227.27; 372/6, 12; 430/311
See application file for complete search history.

(56) References Cited

U.S. PATENT DOCUMENTS

| | | | |
|---|---|---|---|
| 3,979,184 A | 9/1976 | Giaever | 128/2 R |
| 3,985,617 A | 10/1976 | Yugari et al. | |
| 4,350,761 A | 9/1982 | Yamamoto | 435/7.93 |
| 4,592,980 A | 6/1986 | Tomida et al. | 430/59.1 |
| 4,796,981 A | 1/1989 | Nishimura et al. | 359/289 |
| 4,810,639 A | 3/1989 | Pankratz | 435/7.4 |
| 4,819,239 A * | 4/1989 | Sharp et al. | 372/12 |
| 4,828,917 A | 5/1989 | Wegner et al. | 428/333 |
| 4,868,105 A | 9/1989 | Urdea | 435/6 |
| 4,909,990 A | 3/1990 | Block et al. | 422/82.11 |
| 4,933,285 A | 6/1990 | Patton | |
| 5,063,417 A | 11/1991 | Hopfield | |
| 5,246,748 A | 9/1993 | Gillberg-Laforce et al. | 428/1.2 |

(Continued)

FOREIGN PATENT DOCUMENTS
EP   1 288 662 A1   3/2003

(Continued)

OTHER PUBLICATIONS

"Control of Superfine Strucutre of Membrane and Their Characterization", Polymer, vo. 50, Takatoshi, Kinoshita, Department of Engineering, Nagoya Institute of Technology, pp. 648-651, Sep. 2001.

(Continued)

*Primary Examiner*—Phan Palmer
(74) *Attorney, Agent, or Firm*—Sughrue Mion, PLLC

(57) ABSTRACT

Provided are optical switches applicable to various safety apparatuses which can control an operation of a circuit by detecting a switching signal such as pathogens and toxic substances, and safety apparatuses using the optical switches. The optical switch comprises an optical irradiation unit to irradiate light; an optical interference unit which can interact with a switching signal, interferes with light irradiated from the optical irradiation unit and radiates it as interference light, and can vary the wavelength of the interference light after interaction with the switching signal; and a switching unit which is provided in the path of the interference light, detects a wavelength change of the interference light, and conducts one of activating and deactivating a circuit. The safety appatatus comprises the optical switch and a hazard evasive apparatus activating unit which activates a hazard evasive apparatus using the optical switch.

35 Claims, 21 Drawing Sheets

U.S. PATENT DOCUMENTS

| | | | |
|---|---|---|---|
| 5,281,539 A | 1/1994 | Schramm | 204/403.11 |
| 5,304,631 A | 4/1994 | Stewart et al. | |
| 5,354,654 A | 10/1994 | Ligler et al. | 435/5 |
| 5,756,296 A | 5/1998 | Cubicciotti | |
| 5,759,447 A | 6/1998 | Efron et al. | 252/582 |
| 5,766,784 A | 6/1998 | Baskaran et al. | 428/702 |
| 5,783,392 A | 7/1998 | Seibl et al. | 435/6 |
| 5,800,994 A | 9/1998 | Martinelli et al. | 435/6 |
| 5,883,875 A | 3/1999 | Coufal et al. | 369/116 |
| 6,083,689 A | 7/2000 | Martinelli et al. | 435/6 |
| 6,124,963 A | 9/2000 | Schumaker | 359/245 |
| 6,238,864 B1 | 5/2001 | Yan | 435/6 |
| 6,248,539 B1 | 6/2001 | Ghadiri et al. | 435/7.1 |
| 6,261,152 B1 | 7/2001 | Aiyer | 451/6 |
| 6,400,489 B1 | 6/2002 | Suzuki et al. | 359/241 |
| 6,451,543 B1 | 9/2002 | Kochendoerfer et al. | 435/7.1 |
| 6,686,150 B1 | 2/2004 | Blackburn et al. | 435/6 |
| 6,839,175 B1 | 1/2005 | Washizu et al. | |
| 2002/0139961 A1 | 10/2002 | Kinoshita et al. | |
| 2002/0168291 A1 | 11/2002 | Kinoshita et al. | |
| 2002/0168666 A1 | 11/2002 | Kinoshita et al. | |
| 2002/0168667 A1 | 11/2002 | Kinoshita et al. | |
| 2002/0168756 A1 | 11/2002 | Kinoshita et al. | |
| 2003/0003476 A1 | 1/2003 | Kinoshita et al. | 435/6 |
| 2003/0179381 A1 | 9/2003 | Kinoshita et al. | |
| 2004/0156749 A1 | 8/2004 | Washizu et al. | |

FOREIGN PATENT DOCUMENTS

| | | |
|---|---|---|
| GB | 2 245 971 A | 1/1992 |
| GB | 2 245 971 A1 | 1/1992 |
| JP | 63-222248 | 9/1988 |
| JP | 04-009743 | 1/1992 |
| JP | 07/075598 | 3/1995 |
| JP | 9-512345 | 12/1997 |
| JP | 11-183479 | 7/1999 |
| WO | WO 96/26435 | 8/1996 |
| WO | 2000-249644 | 9/2000 |
| WO | WO 01/12665 A2 | 2/2001 |

OTHER PUBLICATIONS

"A Device for Visual Detection of Antigens and Antibodies by Means of Light Inteference", Thin Solid Films, vol. 91, Takeyuki Kawaguchi et al, pp. 369-381, 1990.

Color Tone Control By External Stimuli, Nagoya Institute of Technology, Imitating Function of Bio-skins Applicable to Display Devices, *Nikkan Kogyo Shinbun*, Dec. 28, 2000, Japan.

T. Doi et al., Symposium: Building of Molecular Composition and Its Function, Building and control of peptide type signal transfer function, A506, Nagoya Institute of Technology, Symposium held by JST, Nov. 28, 2000, Japan.

H. Yokoi et al., Preparation of Amphiphilic α-helix LB film, *Polymer Preprints, Japan.* vol. 49 No. 12 IS07, Nagoya Institute of Technology, 2000, Society of Polymer Science, Japan.

H. Yokoi et al., Evaluation of moleuclar orientation of amphiphilic α-helix water surface monomolecular film, *Polymer Preprints, Japan*, vol. 49 No. 13 lipd090, Nagoya Institute of Technology, 2000, Society of Polymer Science, Japan.

Y. Okahata, Sensing of Odorous and Bitter Substances by using a Bilayer Molecular Film-coated Quartz Oscillator, *Biophysics*, vol. 28. No. 6 Pandect, Tokyo Institute of Technology, 1988, Japan.

Y. Okahata, Prospect for Chemical Information Conversion Membrane, Molecular Recognition to be realized on a Lipid Bilayer Molecular Membrane, *SEN-I Gakkaishi (Fiber and Industry)* vol. 46, No. 2 Feature: Functional Macromolecular Membranes Films, 1990, Japan.

K. Ariga et al., Evaluation of the Viscoelasticity of the Membrane with the Use of a Quartz Oscillator, Phase Transition of the LB film, vol. 28 No. 11, Tokyo Institute of Technology, 1990, Japan.

H. Yokoi et al., *The 48th Symposium on Macromolecules*, The Two Dimensional Orientation Control of Amphiphilic α-helix Molecule, II P f094, Nagoya Institute of Technology, Oct. 6, 1999, Niigata, Japan.

H. Yokoi et al., *The 49th Annual Meeting of the Society of Polymer Science, Japan (SPSJ)*, The pH Dependence of Molecular Orientation in Monolayer Composed of Amphiphilic α-helix Molecule at Air-water Interface, I Pg173, Nagoya Institute of Technology, May 29, 2000, Nagoya, Japan.

H. Yokoi et al., *The 49th Symposium on Macromolecules*, Preparation of LB Film consisting of Amphiphilic α-helix Molecule, IS 07, Nagoya Institute of Technology, Sep. 27, 2000, Sendai, Japan.

H. Yokoi et al., *The 49th Symposium on Macromolecules*, "Evaluation of molecular orientation of amphiphilic α-helix water surface monomolecular film", IIPd090, Nagoya Institute of Technology, Sep. 27, 2000, Sendai, Japan.

Y. Nagata, et al., *The 43rd Annual Meeting of the Society of Polymer Science, Japan (SPSI)*, "Preparation and Function of Polypeptide Containing a Substrate-binding Site at the Molecular Terminal", II-9-06, Nagoya Institute of Technology, and National Institute of Materials and Chemical Research, Tsukuba, May 26, 1994, Nagoya, Japan.

H. Hosokawa et al., *The 44th Annual Meeting of the Society of Polymer Science, Japan (SPSI)*, "Functional Control of Polypeptide Containing an Inclusion Terminal Group", II Pel 119, May 30, 1995, Yokohama, Japan.

H. Hosokawa et al., "Functional Control of Polypeptide Containing an Inclusion Terminal Group", Preprints of Annual meeting of the Society of Fiber Science and Technology, Japn, G-264 3G17, Jun. 29, 1995, Tokyo (Sen-I Gakkai).

H. Hosokawa et al., *45th Annual Meeting of Society of Polymer Science of Japan*, Monolayer of polypeptide containing a cyclodextrin at the terminal, IIIPb100, Nagoya Institute Technology, Nagoya and National Institute of Materials and Chemical Research, Tsukuba, May 29, 1996, Nagoya, Japan.

H. Hosokawa et al., *45th Symposium of Society of Polymer Science of Japan*, Molecular orientation polypeptide containing a cyclodextrin at the terminal in the monolayer and its function, 2Pb44, Nagoya Institute of Technology, Oct. 2, 1996, Hiroshima, Japan.

H. Hosokawa et al., *46th Annual Meeting of Society of Polymer Science of Japan*, Structural control of polypeptide containing an active site at the terminal in monolayer and its function, IIPb108, Nagoya Institute of Technology, May 24, 1997, Tokyo, Japan.

A. Kato et al., *47th Annual Meeting of Society of Polymer Science of Japan*, Characterization of polypeptide monolayer containing the molecular recognition site, IIIPd124, Nagoya Institute of Technology, May 29, 1998, Kyoto, Japan.

A. Kato et al., *29th Annual Meeting of Union of Chemistry-Related Societies in Chubu Area, Japan*, Characterization of polypeptide monolayer containing a cyclodextrin at the terminal, 1B0705, Nagoya Institute of Technology, Oct. 3, 1998, Toyohashi, Japan.

H. Yokoi et al., The control of molecular orientation in monolayer of amphiphilic α-helix, *Preprints presented at 15th Symposium of Membrane Science and Technology*, 3PA53, Nagoya Institute of Technology and Core Research for Evolutional Science and Technology, May 12, 1999, Chiba, Japan (Sen-I Gakkai).

T. Doi et al., *48th Symposium of Society of Polymer Science of Japan*, The molecular orientation and oscillation of polypeptide monolayer at oil/water interface, 111J02, Nagoya Institute of Technology and Core Research for Evolutional Science and Technology, Oct. 8, 1999, Niigata, Japan.

T. Doi et al., *Open Symposium of Creation and Functions of New Molecules and Molecular Assemblies sponsored by Core Research for Evolutional Science and Technology (CREST)*, Creation of peptide-type signal transmitting function and control of its function, A506, Nagoya Institute of Technology, Nov. 28, 2000, at Japan Science and Technology Corporation (JST), Tokyo, Japan.

"Molecular alignment of poly(γ-methyl-L-glutamate) containing a β-cyclodextrin at the terminal and molecular identification (n-hexane/water interface)", Control of molecular alignment of polypeptide molecular film published by Dr. Tomokiyo Doi, chapter 4, 2000.

"The Control of Structure and Functions of LB-Film composed of Bio-Related Polymers", First International Symposium on Biometic Materials Processing, Tomokiyo Doi, et al., pp. 19, Jan. 11, 2001.

"Preparation of Structural Color Forming System by Polypeptide-Based LB Films", The fourth NIMC International Symposium on Photoreaction Control and Photofunctional Materials, Takatoshi Kinoshita, pp. 1-9 and 1-12, Mar. 14, 2001.

"Nano-Phase Separation in the Monolayer Composed of α-Helical Copolypeptide at Air/Water Interface," Chemistry Letters 2000, Hidenori Yokoi, et al., pp. 1210-1211, The Chemical Society of Japan.

"The Molecular Recognition and Polypeptide Orientation in the Monolayer at Oil/Water Interface", 12th Academic Symposium of MRS-Japan manuscripts., Dec. 7, 2000, Kanagawa Y. Mouri, et al., p. 66.

"The Molecular Orientation of a Peptide-based Amphiphile at Hexane/Water Interface", Chemistry Letters 1997, Hirofumi Hosokawa, et al., pp. 745-745, The Chemical Society of Japan.

"The guest-induced oscillation of a monolayer composed of polypeptide containing β-cyclodextrin at the terminal", Chaos, vol. 9, No. 2, 1999, T. Kinoshita, et al., pp. 276-282, American Institute of Physics.

"Structural color forming system composed of polypeptide-based LB films", Nanotechnology and Nano-Interface Controlled Electronic Device, T. Kinoshita, et al., pp. 233-252, 2003

"Structural Color with Polypeptide LB Film", Transactions of the Materials Research Society of Japan 27 [3], T. Miyagi, et al., pp. 555-558, 2002.

"Polypeptide membranes at an interface", Prog. Polym. Sci., H. Yokoi, et al., pp. 341-357, 2003.

Thomas M. Cooper, et al., "Formation of Polypeptide-Dye Multilayers by an Electrostatic Self-Assembly Technique," LANGMUIR 1995, vol. 11, No. 7, pp. 2713-2718.

Munekazu Date, et al., "52.3: Direct-viewing Display Using Alignment-controlled PDLC and Holographic PDLC," SID 00 Digest pp. 1184-1187.

Robert J. Collier, et al, "Optical Holography," Chapter 9 §§9.1 & 9.2, pp. 228-233. Academic Press, New York.

Baril et al, "Chromatography of ribonuclease treated myosin extracts from early embryonic chick muscle," Science (1994) 146:413-414.

Liu, et al., "Cell-ELISA using B-galactosidase conjugated antibodies" Journal of Immunological Methods 234 (Feb. 2000) p. 153-167).

Buchel, M. et al., "Langmui-Blodgett-Kuhn Multilayers of Polyglutamates with Azobenzene Moieties: Investigations of Photoinduced Changes in the Optical Properties and Structure of the Films," Langmuir 1995, vol. 11, p. 4460-4466.

Menzel, H. et al., "Small-Angle X-ray Scattering and Ultraviolet-Visible Spectroscopy Studies on the Structure and Structural Changes in Langmuir-Blodgett Films of Polyglutamates with Azobenzene Moieties Tethered by Alkyl Spacers of Different Lengths" Langmuir 1994, vol. 10, p. 1926-1933.

Okahata, Y. et al., "Orientation of DNA Double Strands in a Langmuir-Blodgett Film," Langmuir 1966, vol. 12, p. 1326-1330.

Parazak, D.P. et al., "Comparison of Host-Guest Langmuir-Blodgett Multilayer Formation by Two Different Amphiphilic Cyclodextrins," Langmuir 1996, vol. 12, p. 4046-4049.

Greenham et al, "Charge separation and transport in conjugated-polymer/semiconductor-nanocrystal composites studies by photoluminescence quenching and photconductivity," Physical Review-B, 1996, 54(24), pp. 17628-17637.

Sugai et al., (Poly(γ-alkyl Glutamates), Journal of Polymer Science: Part A-2, vol. 4, 183-198 (1966).

Crick, F.H.C., The Packing of α-Helices: Simple Coiled-Coils, Acta Cryst (1953) 6, 689-697.

Minamoto, Y. et al., Polymethylglutamate as a New Matrix for Covalentaly Immobilized Enzymes: Preparation and Properties of Urease and Uricase, Biotech and Bioeng'n, vol. XXII, pp. 1225-1235 (1980).

* cited by examiner

Capture of detection target

OPTICAL SWITCH AND SAFETY APPARATUS USING THE SAME

BACKGROUND OF THE INVENTION

1. Field of the Invention

The present invention relates to optical switches which can control an operation of a circuit by detecting, as a switching signal, existence of a substance of various kinds such as pathogens, physiological substances, and toxic substances, and which can be applied to various safety apparatuses; and safety apparatuses using the optical switches.

2. Description of the Related Art

To date, many kinds of optical switching circuits have been proposed (see, for example, Japanese Patent Application Laid-Open (JP-A) Nos. 2002-208720 and 2002-350748). However, they employ semiconductors, mirrors, or the like, and none is known that utilizes detecting the change of the wavelength of light. Furthermore, with regards to optical switches which use the wavelength change of light, ones that can control an operation of a circuit by detecting existence of various substances such as pathogens, physiological substances, and toxic substances as a switching signal and that can be applied to various safety apparatuses are yet to be provided.

On the other hand, in waste water treatment processes and the like, the safety of the waste water was achieved by detecting existence of toxic substances by, for example, inspecting the survival of fish such as carp that had been released in a lagoon where the waste water was kept before being released to a river, or by analyzing samples of the waste water at constant intervals. However, these processes had problems including that continuous processing is not possible, that they are complex, and that they do not provide sufficient safety. Although, some safety apparatuses which employ optical switches have been proposed (see, for example, JP-A Nos. 2001-63944 and 10-198426), these are not the ones which operate upon detecting a slight change of wavelength.

Objects and Advantages

An object of the present invention is to provide optical switches which can control an operation of a circuit by detecting, as a switching signal, existence of a substance of various kinds such as pathogens, physiological substances, and toxic substances, and which can be applied to various safety apparatuses.

Another object of the present invention is to provide safety apparatuses which are suitable for hospitals, laboratories, factories, plants, and the like, and which can avoid a hazard by activating a hazard evasive apparatus upon detecting, as a hazard signal, existence of a substance of various kinds such as pathogens, physiological substances, and toxic substances.

SUMMARY OF THE INVENTION

The optical switch of the present invention comprises: an optical irradiation unit to irradiate light; an optical interference unit which can interact with a switching signal, which interferes with light irradiated from the optical irradiation unit and radiates it as interference light, and which can vary the wavelength of the interference light after interaction with the switching signal; and a switching unit which is provided in the path of the interference light, which detects a wavelength change of the interference light radiated by the optical interference unit, and which conducts one of activating and deactivating a circuit. In the optical switch according to the present invention, the optical irradiation unit irradiates light. The optical interference unit interferes with the light irradiated from the optical irradiation unit, and radiates as an interference light. The optical interference unit can interact with the switching signal, and after interacting with the switching signal, the wavelength of the interference light is changed. The switching unit detects the wavelength change of the interference light radiated by the optical interference unit. Then, the switching unit activates or deactivates the circuit. In this manner, the optical switch controls the operation of the circuit.

The safety apparatus of the present invention comprises: an optical irradiation unit to irradiate light; an optical interference unit which can interact with a hazard signal, which interferes with light irradiated from the optical irradiation unit and radiates it as interference light, and which can vary the wavelength of the interference light after interaction with the hazard signal; a wavelength change detecting unit which is provided in the path of the interference light, and which detects a wavelength change of the interference light radiated by the optical interference unit; and a hazard evasive apparatus activating unit which activates a hazard evasive apparatus when the wavelength change detecting unit detects a wavelength change of the interference light. In the safety apparatus according to the present invention, the optical irradiation unit irradiates light. The optical interference unit interferes with the light irradiated from the optical irradiation unit, and radiates as an interference light. The optical interference unit can interact with the hazard signal, and after interacting with the hazard signal, the wavelength of the interference light is changed. The wavelength change detecting unit detects the wavelength change of the interference light radiated by the optical interference unit. The hazard evasive apparatus activating unit activates the hazard evasive apparatus. As a result, hazards are evaded, and safety is secured.

Figure 9:
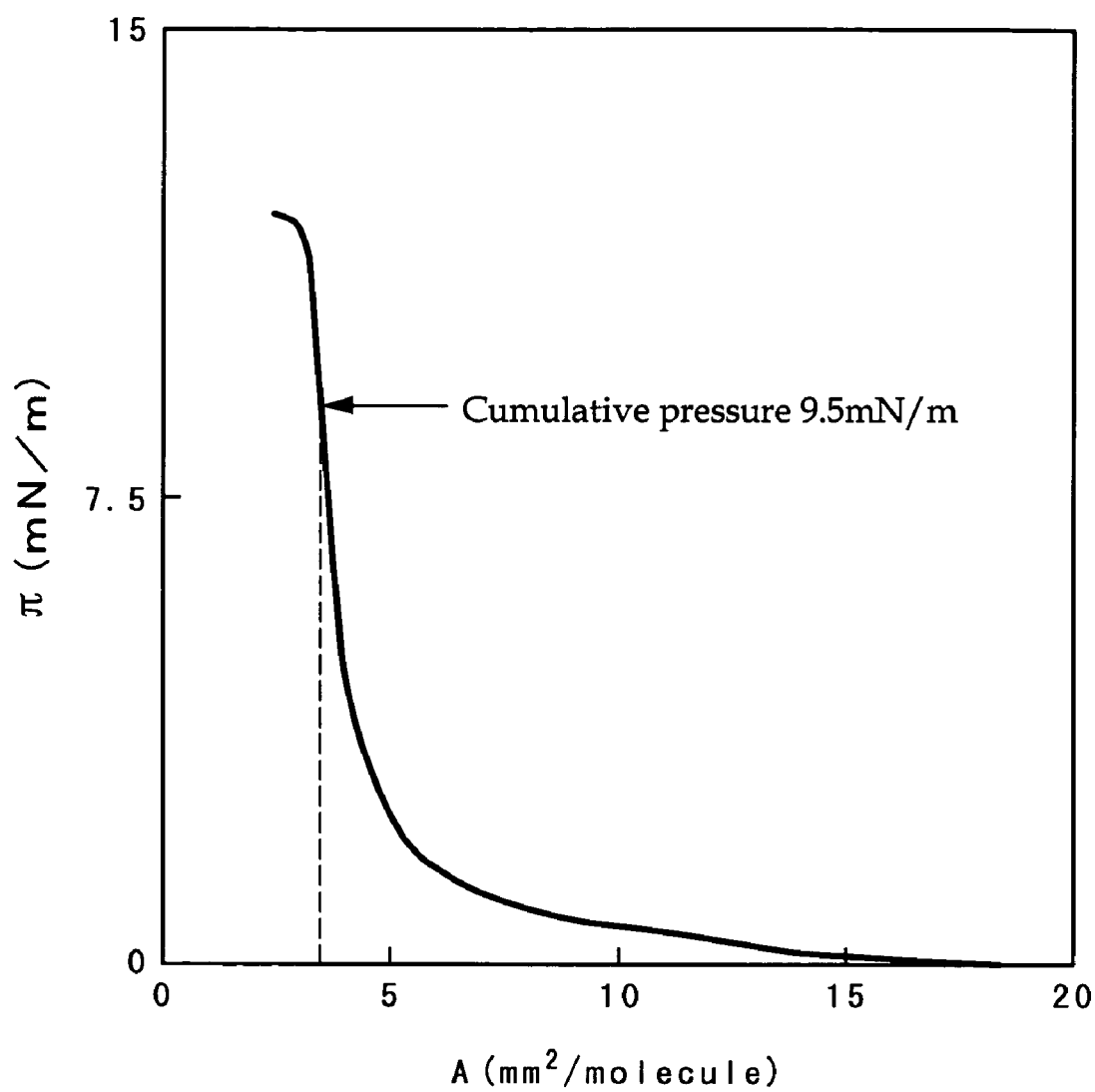

FIG. 9 is a graph showing a cumulative pressure when rod-shaped organic molecules 10 are stacked on a substrate 50 by the LB method.

Figure 10:
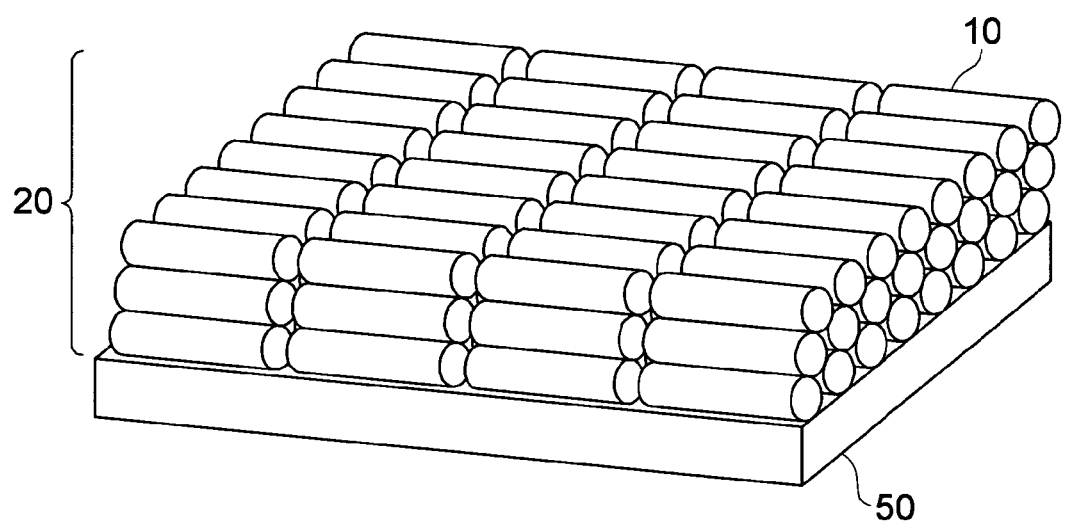

FIG. 10 is a schematic descriptive diagram showing one example of an optical interference unit.

Figure 11:
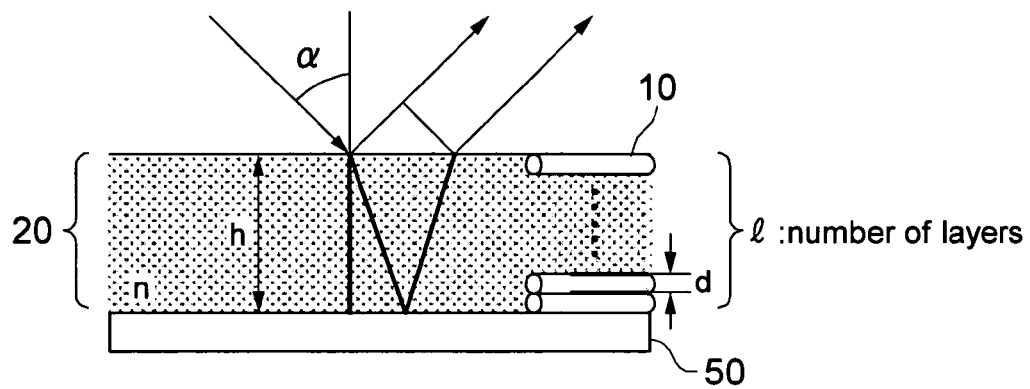

FIG. 11 is a schematic diagram for describing the light interference principle in the optical interference unit.

Figure 12A:
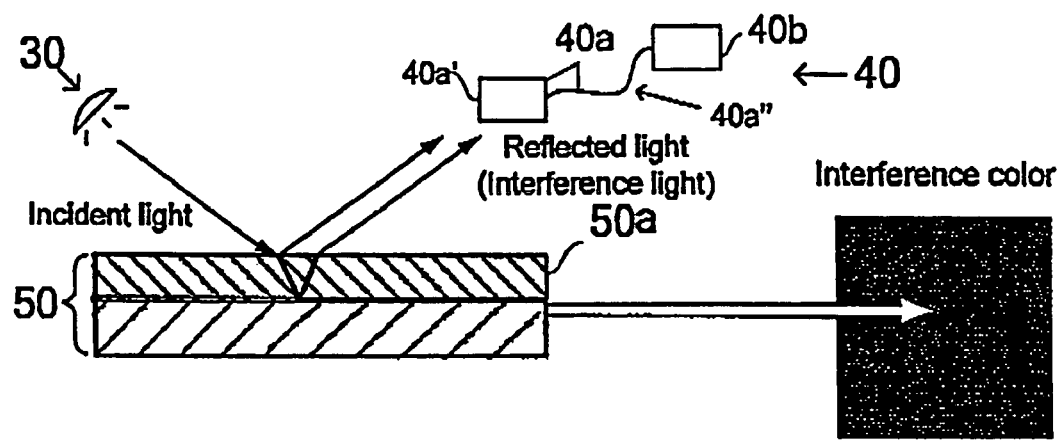
Figure 12B:
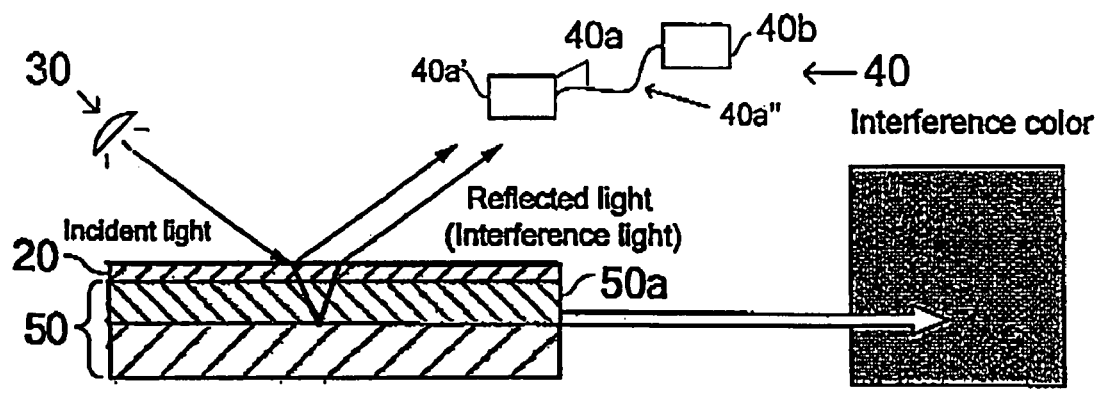

FIG. 12A is a schematic view for describing interference of light and interference color by substrate 50 when film-like material 20 is not provided, and FIG. 12B is a schematic view for describing interference of light and interference color by an optical interference unit having film-like material 20 formed on substrate 50.

Figure 13:
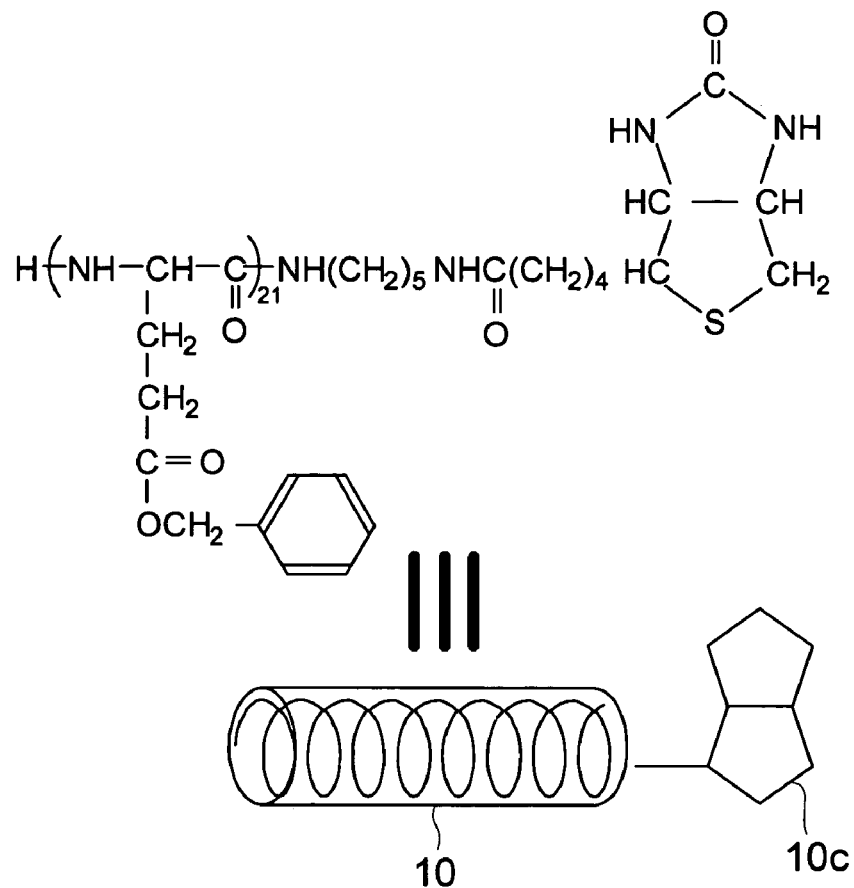
Figure 13:
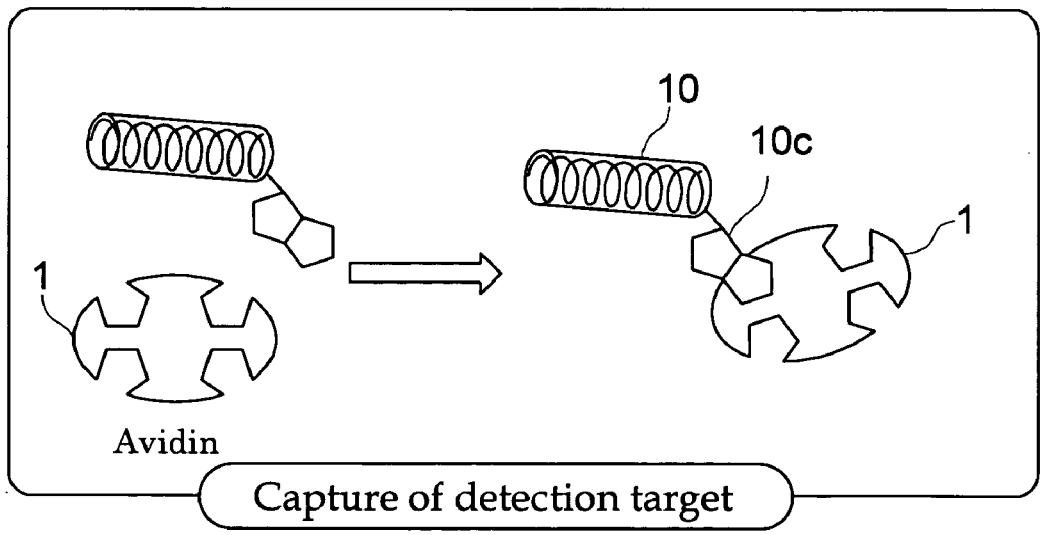

FIG. 13 is a schematic descriptive diagram for describing one aspect of the capture of a switching signal by a signal capturing body provided in the rod-shaped organic molecules.

Figure 14:
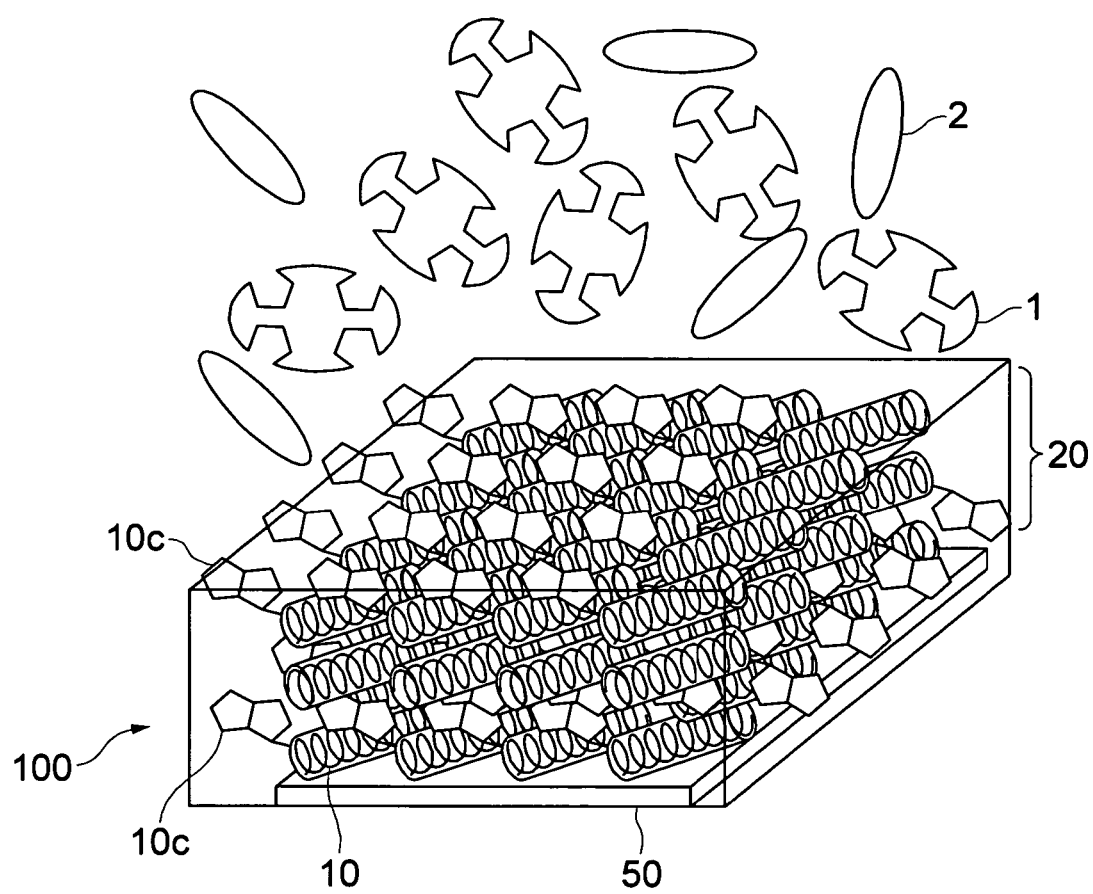

FIG. 14 is a schematic descriptive diagram showing an example of a situation wherein the optical detection unit and a sample containing a switching signal were brought into contact.

Figure 15:
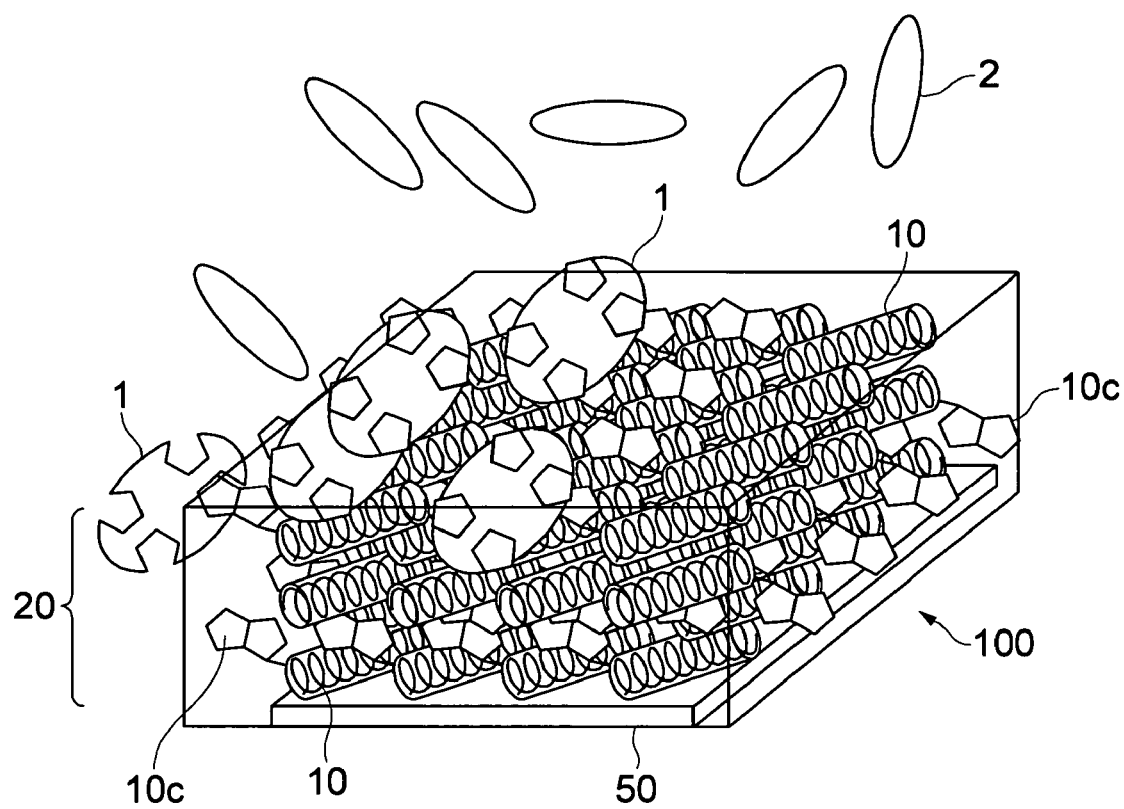

FIG. 15 is a schematic descriptive diagram showing an example of a situation wherein the switching signal was captured by the signal capturing body in the optical detection unit.

Figure 16:
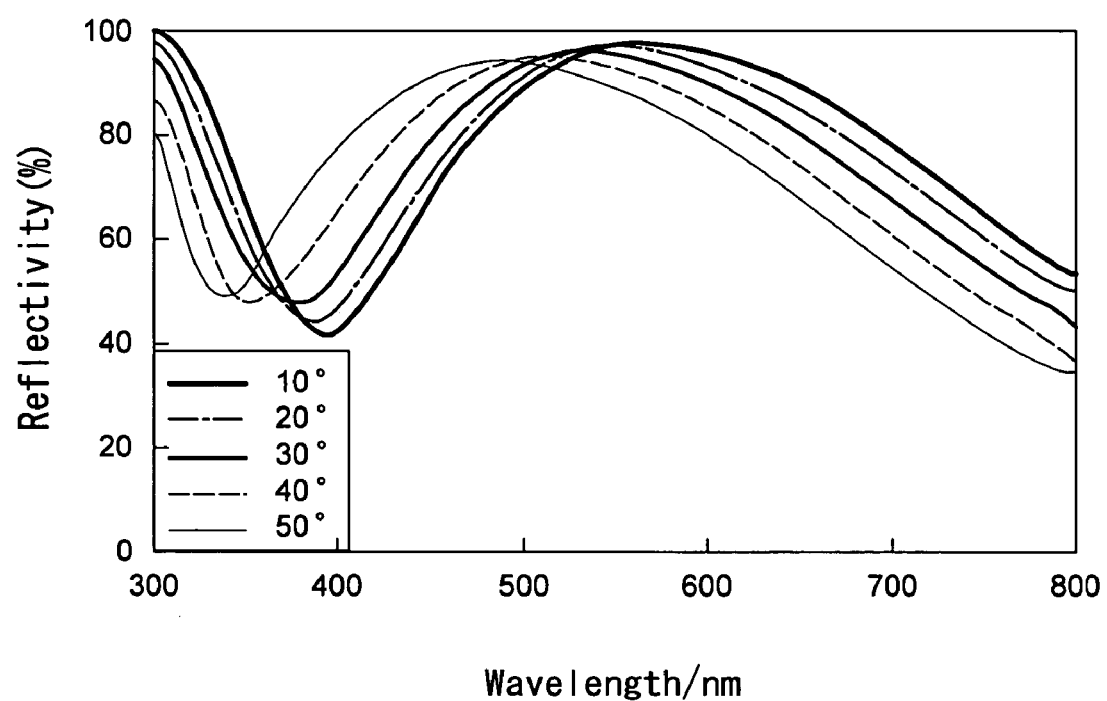

FIG. 16 is a graph of a spectrum showing incidence angle dependency of the intensity of the interference light due to the optical interference unit.

Figure 17:
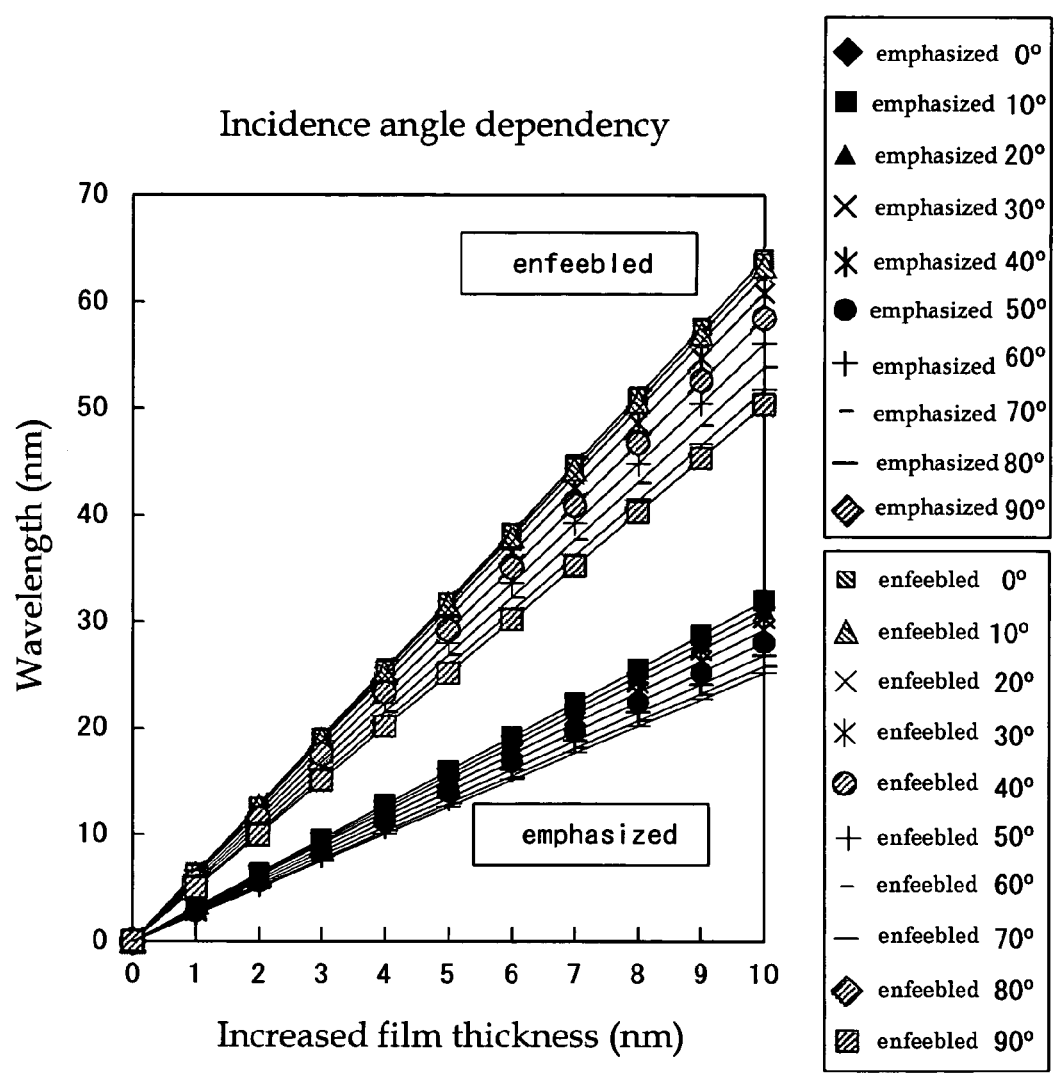

FIG. 17 is a graph showing the relation of interference light intensity to incidence angle and increased thickness of the optical interference unit.

Figure 18:
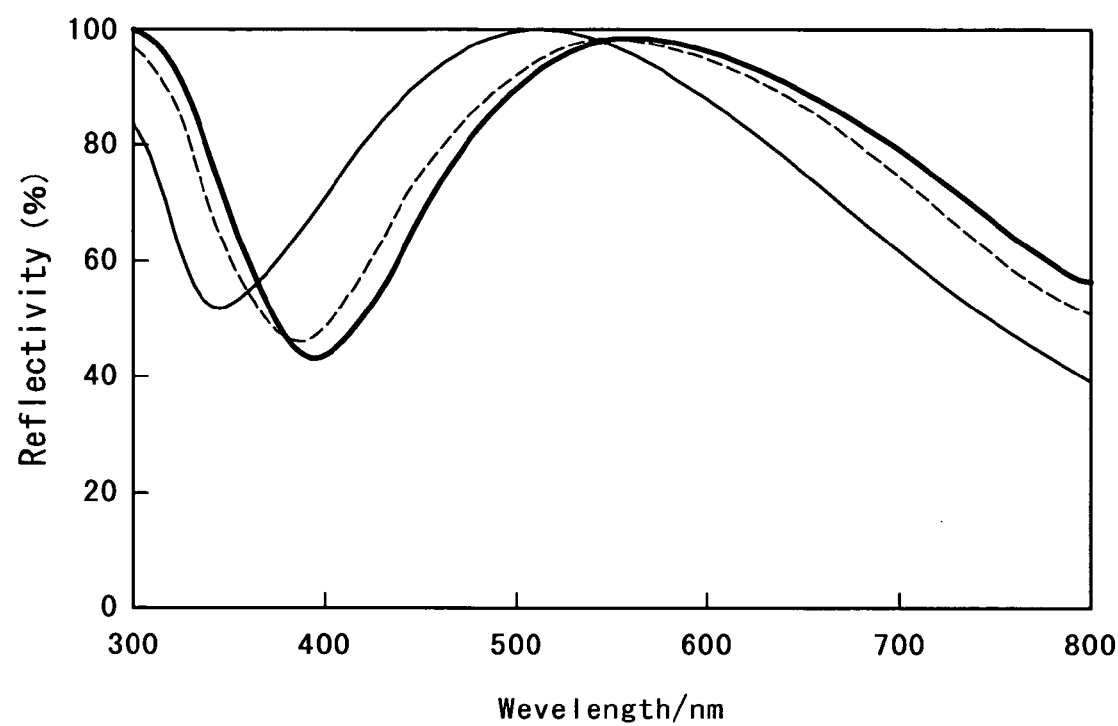

FIG. 18 is a graph showing the spectrum of interference light due to the substrate itself, the spectrum of interference light due to the optical interference unit itself, and the spectrum of interference light when this optical interference unit captures a switching signal.

Figure 19:
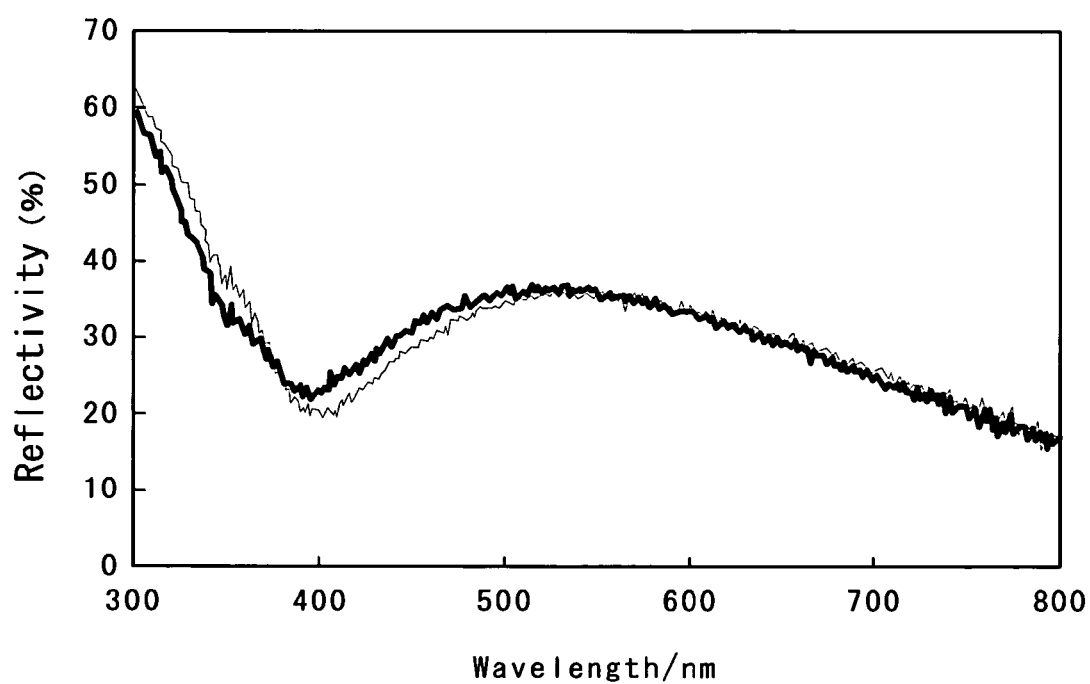

FIG. 19 is a graph showing the spectrum of the interference light due to the optical interference unit, and the spectrum of interference light when the switching signal (avidin) is captured.

Figure 20:
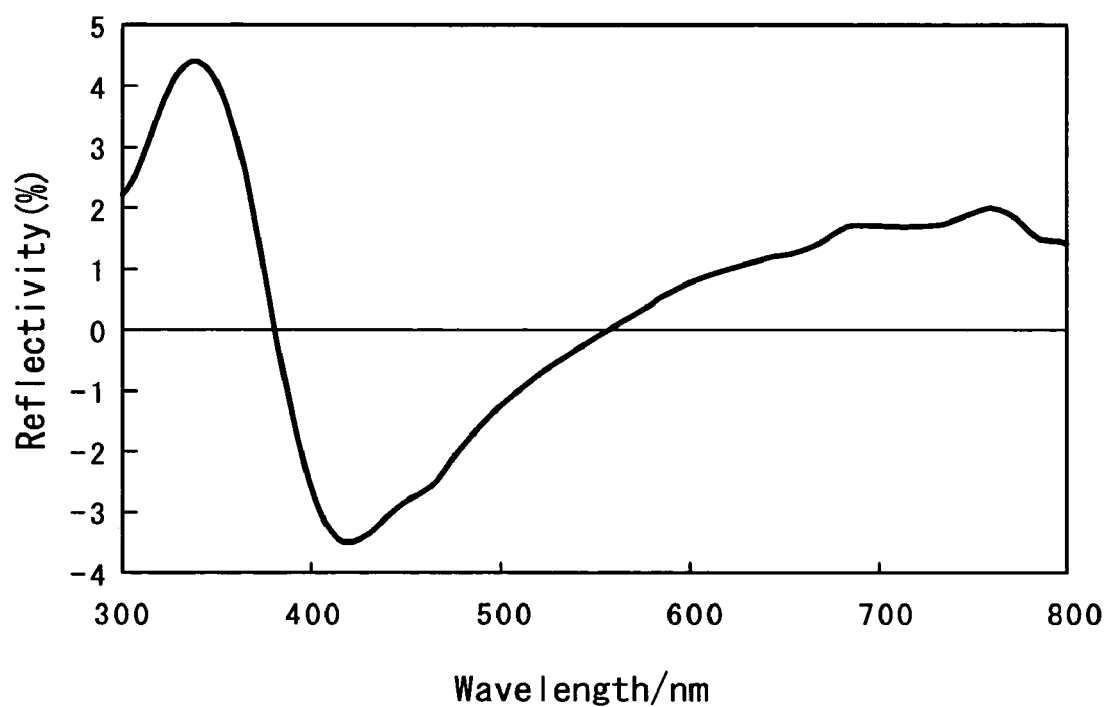

FIG. 20 is a graph showing a differential spectrum when the difference of the two spectral data shown in FIG. 19, is displayed.

Figure 21:
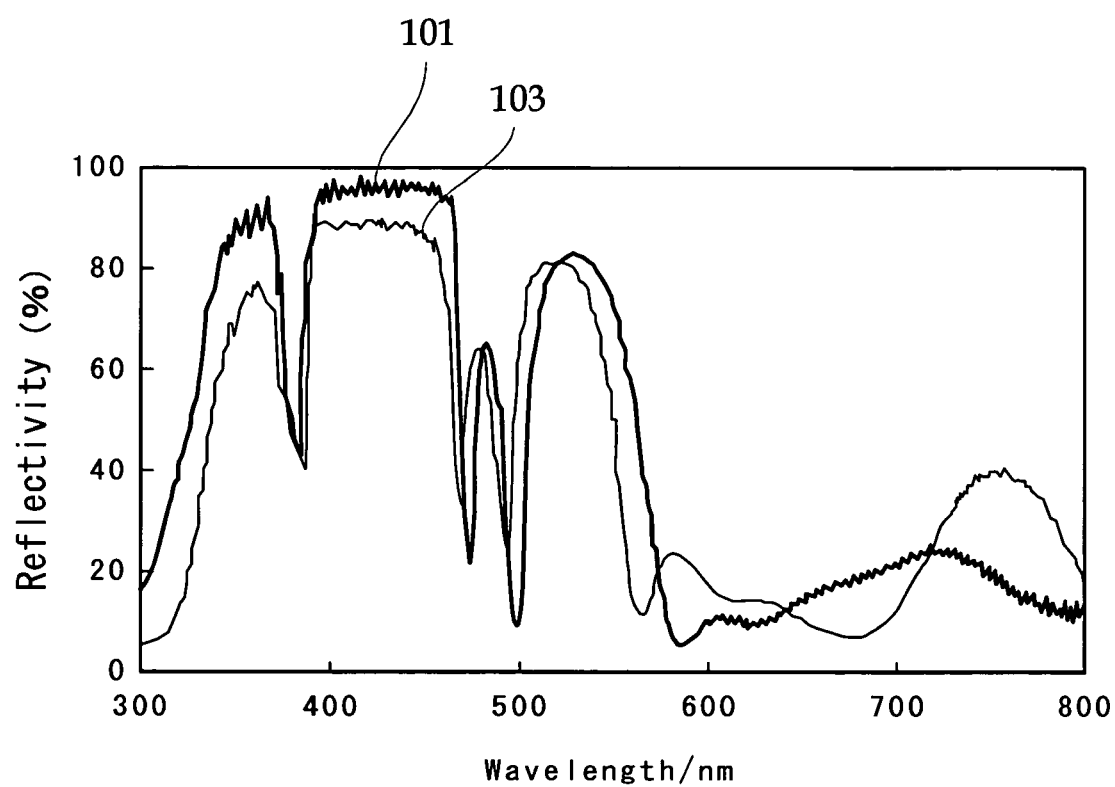

FIG. 21 is a graph showing the spectrum of interference light due to an interference filter, and the spectrum of interference light due to an interference unit formed from this interference filter as a substrate, and a film-like material wherein 88 layers of rod-shaped organic molecules are laminated on the surface thereof.

Figure 22:
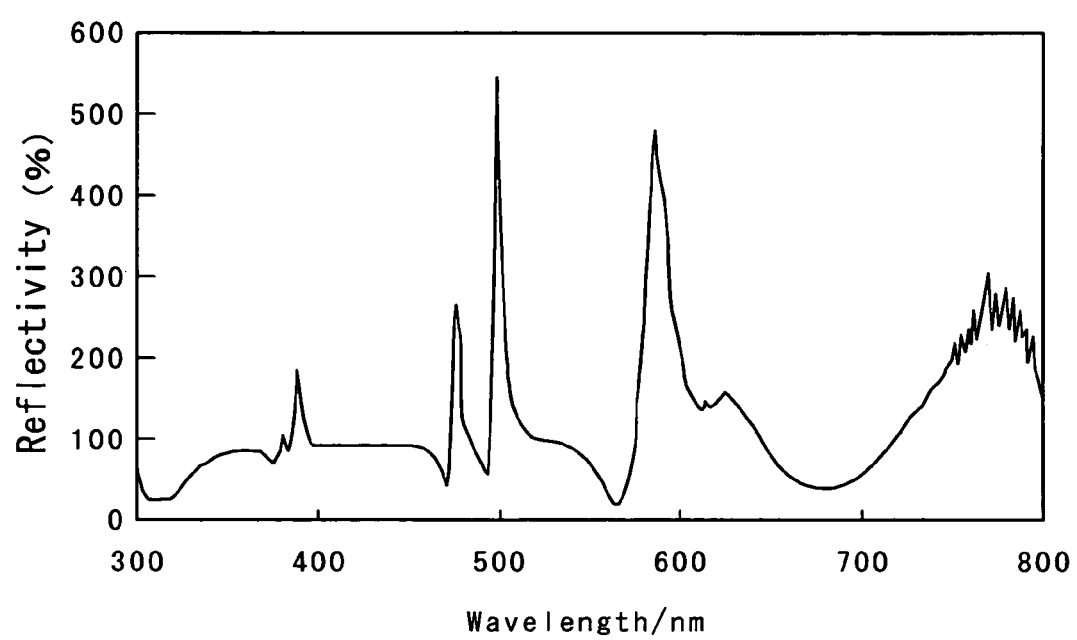

FIG. 22 is a graph showing a differential spectrum when the difference of the two spectra in FIG. 21, is displayed.

DESCRIPTION OF THE PREFERRED EMBODIMENTS (Optical Switch)

The optical switch of the present invention comprises an optical irradiation unit 30, an optical interference unit 20, a switching unit 40 as shown in FIG. 12B, and other unit which may be suitably selected as required.

<Optical Irradiation Unit>

The optical irradiation unit is not particularly limited provided that it irradiates light, and may be selected according to the purpose from light sources known in the art such as for example a halogen lamp (e.g., xenon lamp) or a laser light irradiation device.

Among these, a laser light irradiation device is preferred as it can irradiate a linear luminous flux. In this case, it is easy to control the incidence angle of the light irradiated from this optical irradiation unit to the optical interference unit. Other advantages are that the area of the light-receiving surface in the optical interference unit irradiated by light from the optical irradiation unit can be designed small; that the light-receiving surface of the wavelength change detecting part which detects the wavelength change of the interference light due to the optical interference unit, can be designed small; that measurement noise can be controlled; and that it is possible to prevent switch malfunction effectively.

In the present invention, when a spectrophotometer is used as the wavelength change detecting part, a light source built into this spectrophotometer can be used as the optical irradiation unit.

<Optical Interference Unit>

The optical interference unit has the functions of interfering with the light irradiated from the optical irradiation unit and being able to interact with the switching signal. It interferes with the light irradiated from the optical irradiation unit and radiates it as an interference light, and changes the wavelength of the interference light after interaction with the switching signal. The radiation may be reflected light or transmitted light.

The optical interference unit is not particularly limited as long as it has the functions and can be suitably selected according to the purpose, for example comprising at least a film-like material wherein a rod-shaped material is aligned.

Among these, a film-like material wherein a rod-shaped material is aligned on a substrate is preferred. In this case, as the film-like material is provided on the substrate, the structural stability of this film-like material and surface smoothness are excellent, detection errors can be reduced, and switch malfunction can be prevented.

Substrate

The substrate is not particularly limited as long as the film-like material can be arranged on its surface, and can be selected according to the purpose, but for example, from the viewpoint of reducing detection errors, it preferably has excellent surface smoothness, examples are one or more selected from among semiconductors, ceramics, metals, glass and plastics, or an interference filter or pigment filter. The semiconductor may be selected from among those known in the art, e.g., silicon.

Among these substrates, those comprising an identical refractive index film having a substantially equivalent refractive index to that of the rod-shaped material forming the film-like material on the surface, are preferred. In this case, the thickness of the film-like material which is further provided on this substrate can be made thin, the optical interference unit can be easily manufactured at low cost, and the wavelength of the interference light can be easily adjusted to the visible light region. Depending on the thickness and quality of the material of the oxide film, the interference light due to this substrate may show an interference color, and in this case it can also be used as a "pre-colored substrate".

The thickness of the identical refractive index film varies with the refractive index of the rod-shaped material and cannot be uniquely specified, but it is of the order of 50 nm to 1 μm.

This identical refractive index film can be formed according to methods known in the art, for example vacuum film-forming methods such as the CVD method and PVD method, or thermal oxidation methods. As an example, when the substrate is a silicon substrate, it can be formed as an oxide film by heating this silicon substrate at 900° C. to 1000° C.

Among the substrates, those comprising a different refractive index film having a different refractive index from that of the film-like material on the surface are also preferred. In this case, as the substrate comprises a different refractive index film having a different refractive index from the film-like material on the surface, interference light having a sharp spectral curve can be radiated, and even if the wavelength change (wavelength shift) of this interference light is very small, it can be detected simply, reliably, rapidly and with high sensitivity, and accordingly, this provides an excellent circuit switching performance.

The different refractive index film may also have a different refractive index from that of the substrate and may comprise two or more films, and if there are two or more films, their respective different refractive indices may also be mutually different.

The different refractive index film is not particularly limited and may be suitably selected according to the purpose, but a dielectric film may for example be mentioned.

Materials for the dielectric film include, for example, $TiO_2$, $CeO_2$, $Ta_2O_5$, $ZrO_2$, $Sb_2O_3$, $HfO_2$, $La_2O_3$, $MgO$, $Al_2O_3$, $SiO_2$, $In_2O_3$, $ZnO$, $SnO_2$, $Cd_2SnO_4$, $CdIn_2O_4$, $Zn_2SnO_4$, $ZnSnO_3$, $MgIn_2O_4$, $Zn_2In_2O_5$, and $In_3Sn_3O_{12}$, among which $TiO_2$ and $SiO_2$ are preferable.

The interference filter may be selected from among those known in the art, and commercial filters may also be used. In this case, a sharp interference light with a sharp spectral curve can be radiated, and even if the wavelength change (wavelength shift) of this interference light is very small, it can be detected simply, reliably, rapidly and with high sensitivity, which is advantageous. Also, the thickness of the film-like material further provided on this substrate can be made thin, and as a result, the optical interference unit can be manufactured easily and the optical switch can also be designed as a transmission type apparatus.

The interference filter may be a monochrome filter which extracts a narrow wavelength band (50 nm or less), or it may be a relatively wideband filter such as a dielectric multilayer film, MDM type (e.g., metal/dielectric/metal) or DMD type (e.g., dielectric multilayer film/metal/dielectric multilayer film). In these cases, the dielectric may be formed of an inorganic substance, or may be formed of an organic substance.

In the present invention, the interference filter may also comprise a different refractive index film of different refractive index from the refractive index of the film-like material, on the surface of the substrate.

Film-like Material

The film-like material is not particularly limited and may be suitably selected according to the purpose, for example it may be formed from the rod-shaped material.

The thickness of the film-like material may be suitably selected according to the wavelength of the interference light before and after wavelength change, the refractive index of the substrate, etc., but for example, it is preferably 50 nm to 1 μm.

In the present invention, one or more films may be provided on the surface of the film-like material. This film is not particularly limited and may be selected according to the purpose, but it is preferred that the film has a refractive index which is substantially equivalent to that of the refractive index of the substrate surface in contact with the film-like material. In this case, even an interference light having a sharp spectral curve can be radiated, and even if the wavelength change (wavelength shift) of this interference light is very small, it can be detected simply, reliably, rapidly and with high sensitivity, and this in turn provides an excellent circuit switching performance.

The film is not particularly limited, and may be selected according to the purpose. For example, a dielectric film is preferred.

The dielectric film may be formed on the surface of the film-like material according to, for example, a known process. Specifically, gold, silver, platinum, platinum/palladium, or the like may be selected as materials for the dielectric film, and a thin layer of these materials may be formed by ion coater or the like on the surface of the film-like material. The material of the dielectric is not limited to the above, and may also be an oxide such as silicon oxide.

Rod-shaped Material

The rod material is not particularly limited and can be suitably selected according to the purpose, for example a rod-shaped inorganic molecule or a rod-shaped organic molecule.

One of these may be used alone, or two or more may be used together. Among these, a rod-shaped organic molecule is preferred from the viewpoints that it easily interacts with the switching signal, molecular treatment is easy, formation of the film-like material is easy, and even if the surface quality of the undersurface of the film-like material is not smooth, the surface on the opposite side can easily be maintained smooth.

The rod-shaped organic molecule is not particularly limited and can be suitably selected according to the purpose, e.g., a biopolymer or a polysaccharide.

Examples of the biopolymer are a fibrous protein, an α-helix polypeptide and a nucleic acid (DNA, RNA). Examples of this fibrous protein are those having an α-helix structure such as α-keratin, myosin, epidermin, fibrinogen, tropomycin and silk fibroin.

The polysaccharide may for example be amylose or the like.

From the viewpoint of maintaining the stability rod-shape of the organic molecule, a helical molecule wherein the molecule has a helical structure is preferred. In this case, even if the surface quality (e.g., the surface quality of the substrate) of the undersurface of the film-like material is not smooth, the surface (upper surface) (surface on which light is incident from the optical irradiation unit) on the opposite side can easily be maintained smooth, and measurement errors of wavelength variation produced when the surface is not smooth, can be reduced, and this in turn provides an excellent circuit switching performance.

Among those mentioned above, the spiral molecule may be an α-helix polypeptide, DNA, amylose, etc.

α-Helix Polypeptide

The α-helix polypeptide is one of the secondary structures of a polypeptide. It is rotated once (forms one spiral) every 3.6 aminoacid residues, forms substantially parallel hydrogen bonds with the spiral axis between the imido group (—NH—) and carbonyl group (—CO—) every fourth aminoacid, and has a structure which is stable energywise due to the repetition of 7 aminoacids as one unit.

The direction of the helix of the α-helix polypeptide is not particularly limited, and may be right-handed or left-handed. Due to stability factors, only α-helix polypeptides having a right-handed helix are found in nature.

The aminoacid which forms the α-helix polypeptide is not particularly limited and may be selected according to the purpose if it can form an α-helix structure. Aminoacids which can easily form this α-helix structure are preferred, examples of such aminoacids being aspartic acid (Asp), glutamic acid (Glu), arginine (Arg), lysine (Lys), histidine (His), asparagine (Asn), glutamine (Gln), serine (Ser), threonine (Thr), alanine (Ala), valine (Val), leucine (Leu), isoleucine (Ile), cysteine (Cys), methionine (Met), thyrosin (Tyr), phenylalanine (Phe) and tryptophan (Trp). One of these may be used alone, or two or more may be used together.

By suitably selecting the aminoacid, the α-helix polypeptide can be designed to have hydrophilicity, hydrophobicity or amphiphilicity. If hydrophilicity is conferred, the aminoacid may for example be serine (Ser), threonine (Thr), aspartic acid (Asp), glutamic acid (Glu), arginine (Arg), lysine (Lys), asparagine (Asn) or glutamine (Gln). If hydrophibicity is to be conferred, the aminoacid may for example be phenylalanine (Phe), tryptophan (Trp), isoleucine (Ile), thyrosin (Tyr), methionine (Met), leucine (Leu) or valine (Val).

The aminoacid forming the α-helix polypeptide is not particularly limited, and may for example be a L-amino acid or D-amino acid, or a derivative thereof wherein the side chains are modified.

In the α-helix polypeptide, by esterifying the carboxyl group in the amino acid which forms this α-helix which does not form a peptide linkage, hydrophobicity can be conferred by esterification, or hydrophilicity can be conferred by hydrolyzing this esterified carboxyl group.

The number of linkages (polymerization degree) of the aminoacid in the α-helix polypeptide is not particularly limited and can be suitably selected according to the purpose, but it is preferably 10 to 5000.

If the number of linkages (polymerization degree) is less than 10, the polyaminoacid may not be able to form a stable α-helix, and if the number of linkages (polymerization degree) is more than 5000, it may become difficult to orient it in a perpendicular direction.

Examples of the α-helix polypeptide are polyglutamic acid derivatives such as poly(γ-methyl-L-glutamate), poly(γ-ethyl-L-glutamate), poly(γ-benzyl-L-glutamate), poly(L-glutamine acid-γ-benzyl) and poly (n-hexyl-L-glutamate), polyaspartic acid derivatives such as poly(β-benzyl-L-aspartate), poly(L-leucine), poly(L-alanine), poly(L-methionine), poly(L-phenylalanine), and poly(L-lysine)-poly(γ-methyl-L-glutamate).

The α-helix polypeptide may be suitably be synthesized or prepared by a method known in the art, or the commercial product may be used.

As an example of the synthesis of the α-helix polypeptide, the block copolypeptide [poly(L-lysine)$_{25}$-poly(γ-methyl-L-glutamate)$_{60}$] PLLZ$_{25}$-PMLG$_{60}$ may be synthesized as follows. The block copolypeptide [poly(L-lysine)$_{25}$-poly(γ-methyl-L-glutamate)$_{60}$] PLLZ$_{25}$-PMLG$_{60}$, is synthesized by polymerizing N$^\epsilon$-carbobenzoxy L-lysine N$^\alpha$-carboxylic acid anhydride (LLZ-NCA) using n-hexylamine as initiator, and then polymerizing γ-methyl L-glutamate N-carboxylic acid anhydride (MLG-NCA) as shown by the following formula:

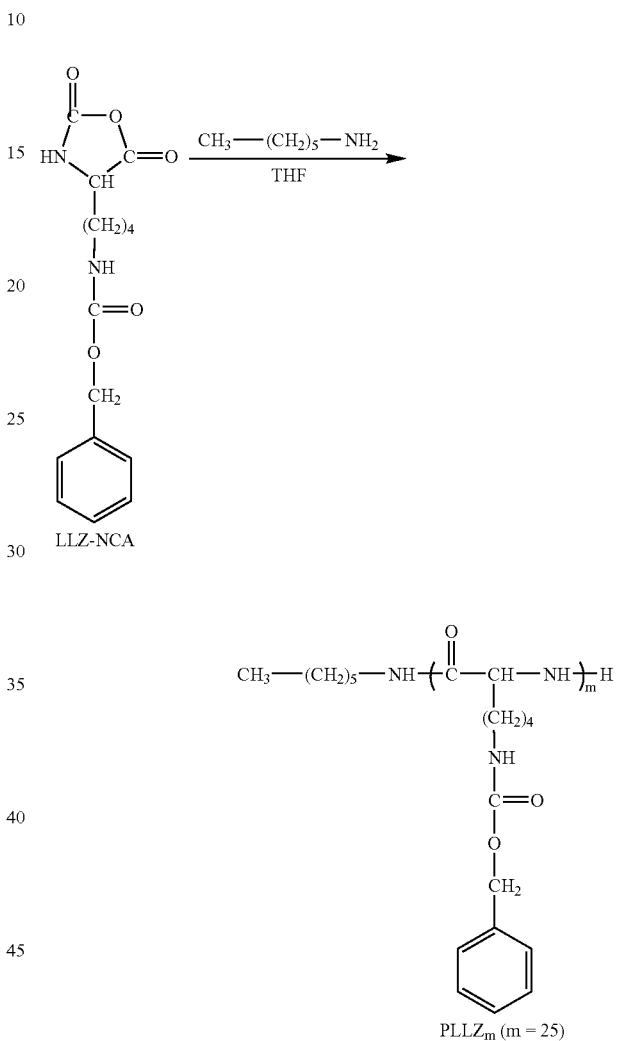

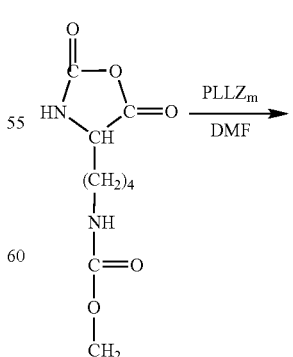

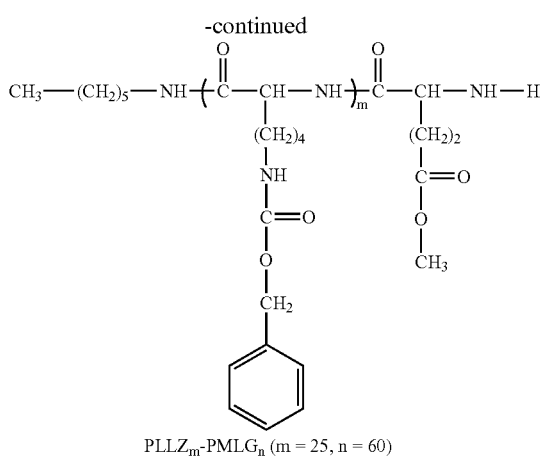

PLLZ$_m$-PMLG$_n$ (m = 25, n = 60)

The synthesis of the α-helix polypeptide is not limited to the above, and can also be achieved by genetic engineering. For example, a host cell is transformed by an expression vector incorporating DNA which codes for the polypeptide, and this transformant is then cultured.

Examples of this expression vector are a plasmid vector, a phage vector, or the chimera vector of a plasmid and phage.

Examples of the host cell are prokaryon microorganisms such as *Escherichia coli* and *Bacillus subtilis*, eukaryon microorganisms such as yeast fungus, and animal cells.

The α-helix polypeptide may also be prepared by cutting out the α-helix structure portion from natural fibrous proteins such as α-keratin, myosin, epidermin, fibrinogen, tropomycin and silk fibroin.

DNA

The DNA may be single-stranded DNA, but from the viewpoint of stabilizing the rod shape, it is preferred that it is double-stranded DNA.

The double-stranded DNA has a double helix structure wherein two right-handed helical polynucleotide chains are positioned so that they extend in mutually opposite directions around one central axis.

The polynucleotide chain is formed by four kinds of nucleic acid bases, i.e., adenine (A), thymine (T), guanine (G) and cytosine (C). In the polynucleotide chain, the nucleic acid bases mutually project inside a plane perpendicular to the central axis, forming the so-called Watson-Crick base pairs wherein thymine is specifically hydrogen-bonded to adenine, and cytosine is specifically hydrogen-bonded to guanine, respectively. As a result, in the double-stranded DNA, two polypeptide chains are joined together complementarily.

The DNA can be prepared by the PCR (Polymerase Chain Reaction) method, the LCR (Ligase Chain Reaction) method, the 3SR (Self-sustained Sequence Replication) method and the SDA (Strand Displacement Amplification) method known in the art, but among these, the PCR method is preferred.

The DNA may be directly cut out enzymatically with a restriction enzyme, prepared by a gene cloning method, or prepared by a chemosynthesis method.

In the case of the gene cloning method, the DNA can be prepared in large amounts by incorporating the product of amplifying a normal nucleic acid into a vector selected from a plasmid vector, a phage vector or the chimera vector of a plasmid and phage, and introducing it into an arbitrary host capable of multiplication selected from a prokaryon microorganism such as *Escherichia coli* or *Bacillus subtilis*, eukaryon microorganism such as yeast fungus, or animal cells.

The chemosynthesis method may be a liquid phase process such as the triester method and phosphorous acid method, or a solid phase synthetic process using an insoluble carrier. In the case of the chemosynthesis method, after preparing single-stranded DNA in large amount using an automatic synthesis machine known in the art, double-stranded DNA can be prepared by performing annealing.

Amylose

The amylose is a polysaccharide having a helical structure wherein D-glucose which forms starch, a homopolysaccharide for storing higher plants, is connected in a straight chain by α-1,4 bonds.

The molecular weight of the amylose is preferably of the order of from several thousands to about 150,000 in terms of number average molecular weight.

The amylose may be a commercial product, or may be suitably prepared according to a known method.

Part of the amylose may also contain amylopectin.

The length of the rod-shaped organic molecule is not particularly limited, and can be suitably selected according to the purpose.

The diameter of the rod-shaped organic molecule is not particularly limited, but in the case of the α-helix polypeptide, it is of the order of 0.8 nm to 2.0 nm.

The rod-shaped organic molecule may be completely lipophilic (hydrophobic), hydrophilic, or amphiphilic wherein part is lipophilic (hydrophobic) or hydrophilic, and the other part has the opposite affinity to this part.

The wavelength of the interference light due to the optical interference unit may or may not be in the visible light region. The former case is preferred as the wavelength of the interference light can be detected visually, and it is more preferred that the wavelength of the interference light is in the visible light region after wavelength change. In this case, this interference light can be observed as an interference color, the principle whereby this interference color is observed being based on so-called structural color formation.

Structural Color Formation

Reflection of the incident light as the colored interference light is a color formation (color of interference light) in which, when an external stimulus, such as an electric field, a magnetic field, heat, light (e.g., natural light, infrared light, ultraviolet light), or the like, is applied to the film, light of a specific wavelength is reflected in accordance with the thickness of the film and the refractive index thereof, on the basis of the multilayer thin-film interference theory which is the basic principle of color formation of the scaly powder of the wings of a Morpho butterfly. As a result, color formation (colored interference light) occurs at the surface of the film. In the structural color formation, a dye or pigment is unnecessary.

Hereinafter, the principles of light reflection of incident light as colored interference light will be explained.

Figure 1:
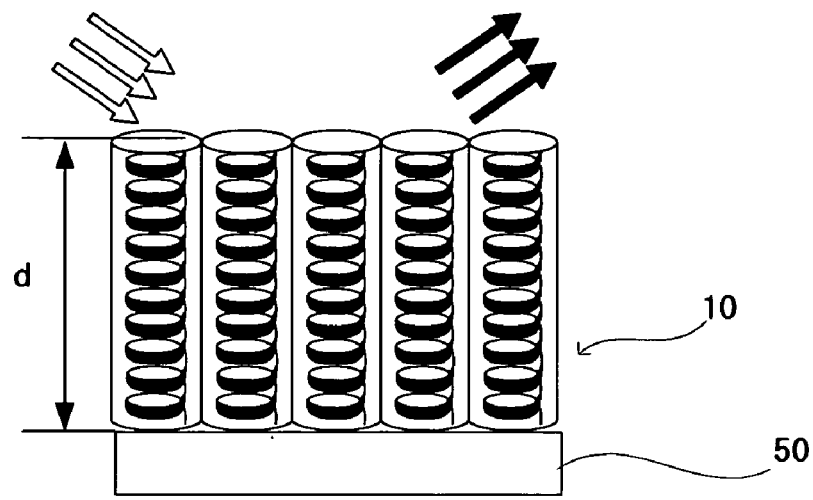
FIG. 1 is a schematic view for explaining structural color formation (occurrence of an interference color) by a monomolecular film (film-like material) of rod-shaped organic molecules (rod-shaped materials) provided on a substrate.
Figure 2:
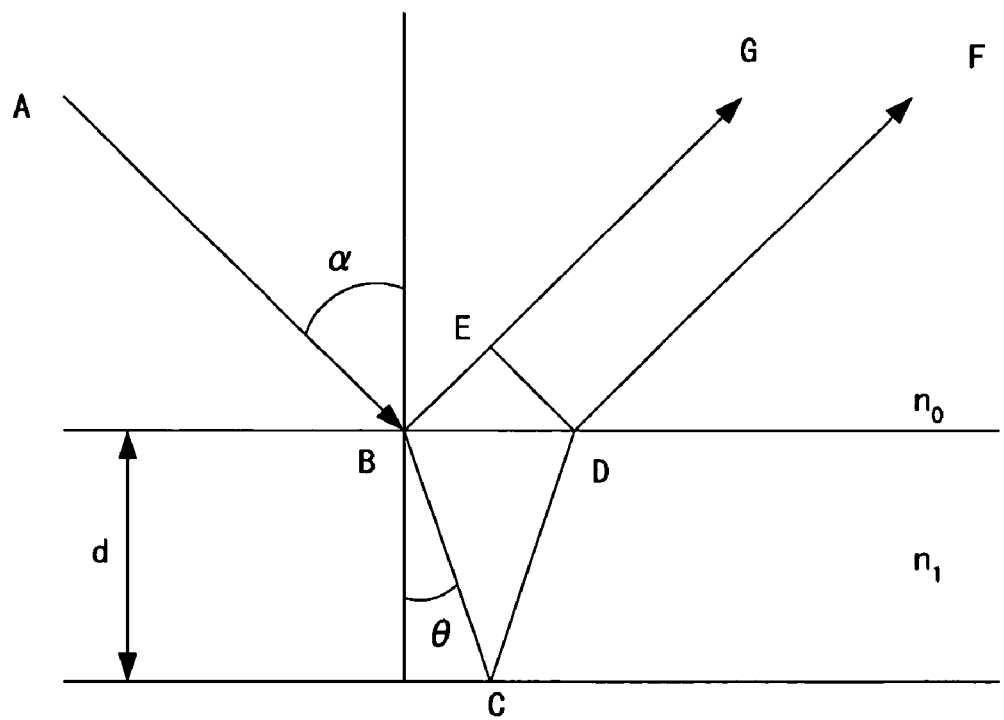
FIG. 2 is a schematic view for explaining the principles of structural color formation.

As shown in FIGS. 1 and 2, the wavelength (λ) of the interference light due to this film-like material (or film-like material formed of the rod-shaped material 10 and oxide layer in the substrate 50) when the film-like material (or film-like material formed of the rod-shaped material 10 and oxide layer in the substrate 50), is irradiated by the optical irradiation unit, is emphasized under the conditions shown in the following mathematical formula (1), and enfeebled under the conditions shown in the following mathematical formula (2).

$$\lambda = \frac{2tl}{m}\sqrt{n^2 - \sin^2\alpha} \quad (1)$$

$$\lambda = \frac{4tl}{2m - 1}\sqrt{n^2 - \sin^2\alpha} \quad (2)$$

In mathematical formula (1) and mathematical formula (2), λ is the wavelength (nm) of interference light, α is the incidence angle (°) of light on the film-like material (or film-like material formed of the rod-shaped organic molecules 10 and oxide layer in the substrate 50), "t" is the thickness (nm) of the film-like material (or the film-like material and the oxide layer in the substrate), "l" is the number of the film-like materials (or film-like material and oxide layer in the substrate), "n" is the refractive index of the film-like material (or film-like material formed of the rod-shaped organic molecules 10 and oxide layer in the substrate 50), and "m" is an integer equal to 1 or more.

The thickness of the film-like material (or film-like material formed of the rod-shaped organic molecules 10 and oxide layer in the substrate 50), is preferably 810 nm or less, but more preferably 10 nm to 810 nm.

By suitably changing the thickness, the color (wavelength) of the structural color can be changed.

The film-like material may be a monomolecular film-like material of the rod material, or may be a laminated film-like material of this monomolecular film-like material.

The monomolecular film-like material or the laminated film-like material may be formed for example by a coating method known in the art, or Langmuir-Blodgett's technique (LB method).

In the former case, among the coating methods known in the art, spin coating is preferable for its ease of operation, and, when the film-like material is formed with a rod-shaped material, it is advantageous for its ability to form the film-like material efficiently by self-organization based on liquid crystallinity of the rod-shaped material or by self-organization based on interaction between a terminal functional group of the rod-shaped material and the substrate.

In the latter case, an LB film-forming apparatus known in the art (e.g., NL-LB400 NK-MWC, Japan Laser & Electronics Laboratories) can be used.

Figure 3:
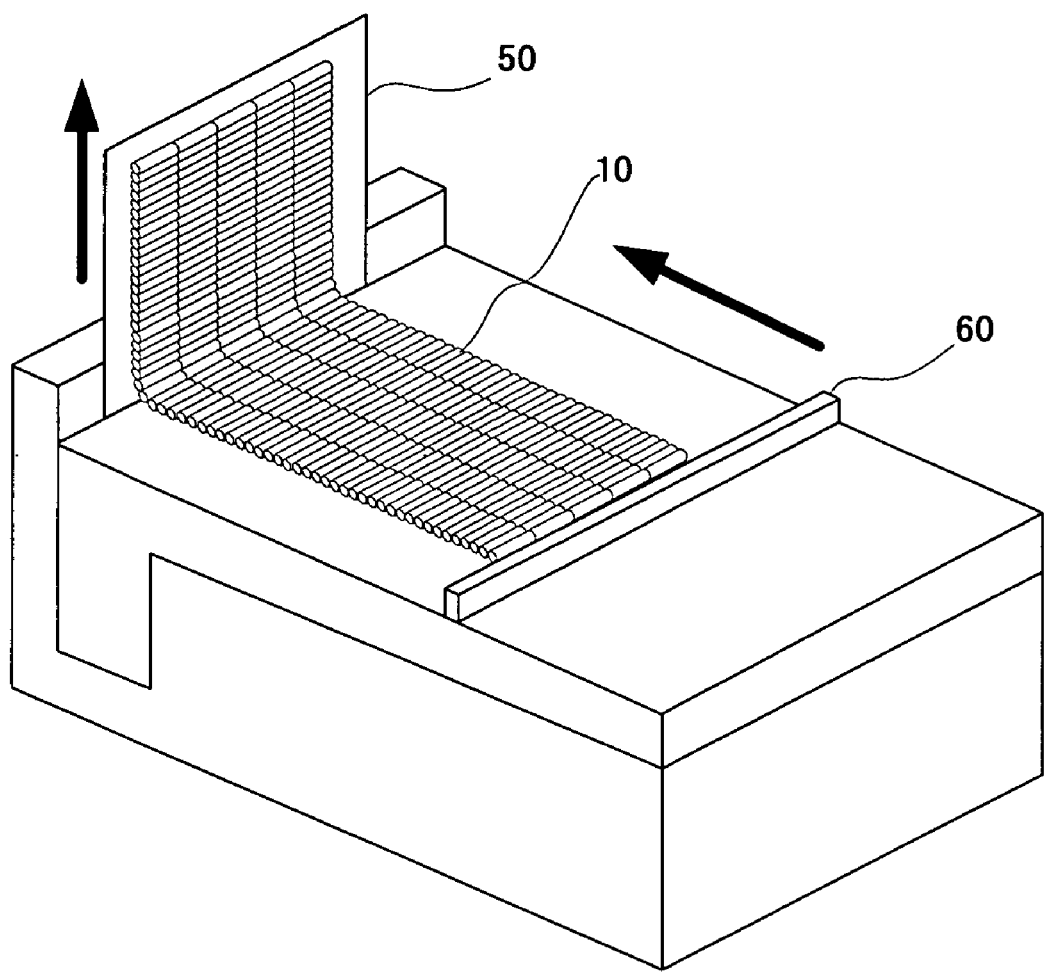
FIG. 3 is a schematic descriptive diagram showing one example of the formation of a monomolecular film (film-like material) by rod-shaped organic molecules (LB method).

The monomolecular film-like material can be formed on the substrate 50 using an extrusion member 60, for example in the state where lipophilic (hydrophobic) or amphiphilic rod-shaped organic molecules are floating on a water surface (aqueous phase), or the state where hydrophilic or amphiphilic rod-shaped organic molecules are floating on an oil surface (oil phase), i.e., a state wherein the rod-shaped organic molecules 10 are oriented as shown in FIG. 3. By repeating this operation, a laminated film comprising a desired number of monomolecular films can be formed on the substrate 50.

At this time, it is preferred to give the surface of the substrate 50 a surface treatment such as hydrophilic treatment and lipophilic treatment for the purpose of making the rod-shaped organic molecules 10 adhere or bond, for example if the rod-shaped organic molecule 10 (e.g., an α-helix polypeptide) is hydrophilic, it is preferred to first perform a surface treatment beforehand, such as hydrophilization treatment using octadecyl trimethylsiloxane or the like. When the surface of the substrate 50 is treated to be hydrophilic, the rod-shaped organic molecules 10 can be arranged vertically on the substrate 50, and when the surface of the substrate 50 is treated to be hydrophobic, the rod-shaped organic molecules 10 can be arranged horizontally on the substrate 50. The hydrophilic treatment and lipophilic treatment are performed using, for example, a coupling agent.

Figure 4:
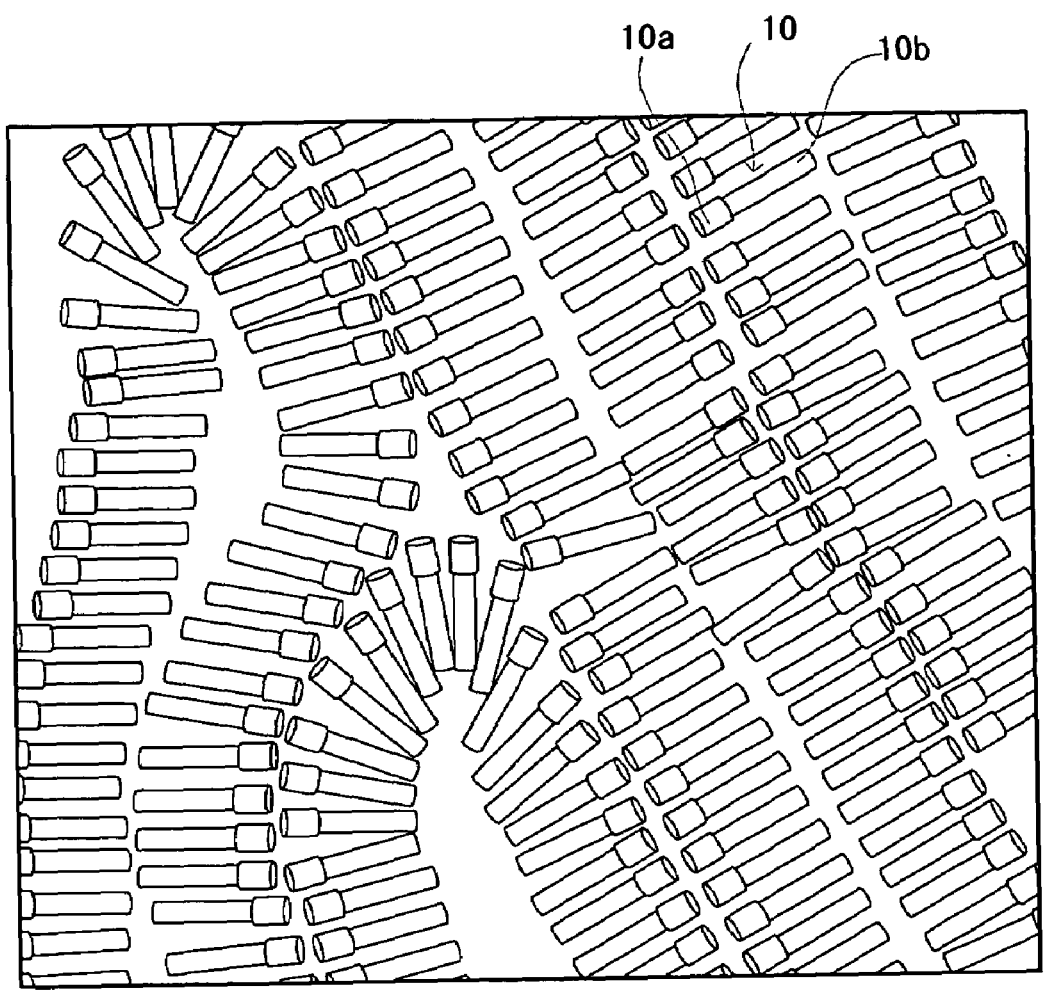
FIG. 4 is a schematic descriptive diagram showing an example of how amphiphilic rod-shaped organic molecules are oriented on water (or an aqueous phase).

When the monomolecular film of amphiphilic rod-shaped organic molecules 10 is formed, the state wherein the rod-shaped organic molecules 10 float on the oil phase or aqueous phase is such that the lipophilic parts (hydrophobic parts) 10a are oriented adjacent to each other, and the hydrophilic parts 10b are oriented adjacent to each other in the rod-shaped organic molecules 10 on the aqueous phase or oil phase, as shown in FIG. 4.

Figure 5A:
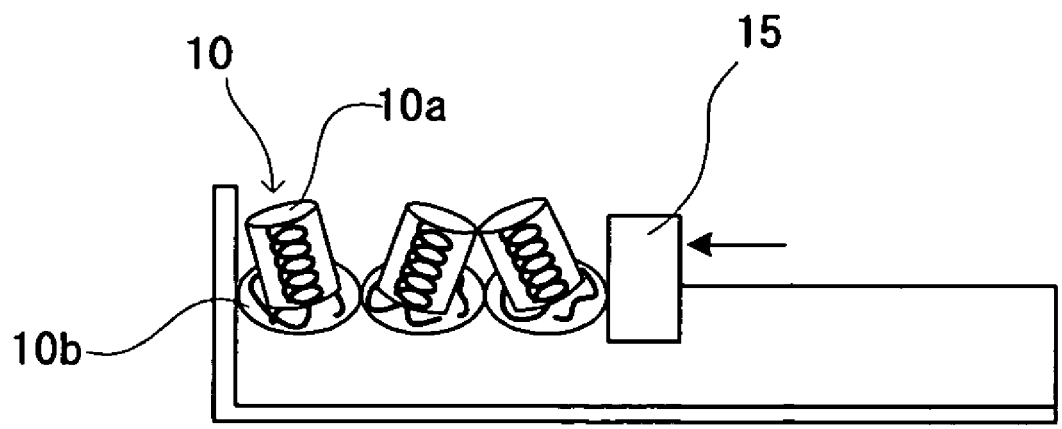
FIGS. 5A and 5B are schematic descriptive diagrams showing an example of a method for standing amphiphilic rod-shaped organic molecules on water (or an aqueous phase).
Figure 5B:
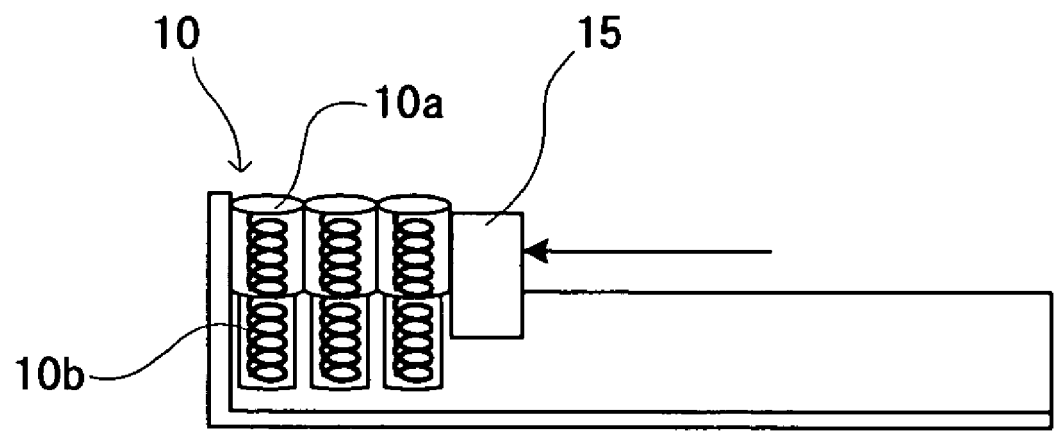

Described above is an example of a monomolecular film wherein the rod-shaped organic molecules are oriented in the plane direction of the monomolecular film (laid horizontally) or a laminated film comprising monomolecular films. A monomolecular film wherein the rod-shaped organic molecules are oriented in the thickness direction of the monomolecular film (standing state) can for example be formed as described below. Specifically, as shown in FIGS. 5A and B, first, the pH of the water (aqueous phase) is adjusted to an alkalinity of about 12 with the amphiphilic rod-shaped organic molecules 10 (α-helix polypeptide) floating on the water surface (aqueous phase). As a result, the hydrophilic parts 10b of the rod-shaped organic molecules 10 (α-helix polypeptide) lose the α-helix structure and take up a random configuration. At this time, the lipophilic parts (hydrophobic parts) 10a of the rod-shaped organic molecules 10 (α-helix polypeptide) retain their α-helix structure. Next, the pH of the water (aqueous phase) is adjusted to an acidity of about 5. As a result, the hydrophilic parts 10b of the rod-shaped organic molecules 10 (α-helix polypeptide) again take up an α-helix structure. At this time, when a pressure member 15 brought into contact with the rod-shaped organic molecules 10 (α-helix polypeptide), the pressure member 15 presses the rod-shaped organic molecules 10 (α-helix polypeptide) by air pressure from the side in the direction indicated by the arrows in FIGS. 5A and 5B, and the rod-shaped organic molecules 10 remain standing on the water (aqueous phase) and the hydrophilic parts 10b become oriented effectively perpendicular to the water surface in the aqueous phase to take up an α-helix structure. Hence, as described above referring to FIG. 3, a monomolecular film can be formed on a substrate 50 by extruding on the substrate 50 using a pressure member 60 with the rod-shaped organic molecules 10 (α-helix polypeptide) aligned in an orderly manner. By repeating this operation, a laminated film comprising a desired number of monomolecular films can be formed on the substrate 50.

Signal Interaction Part

In the present invention, it is preferred that the rod-shaped material comprises a signal interaction part which is capable of interaction with the switching signal. In this case, due to the interaction of this signal interaction part of the rod-shaped material with the switching signal, a wavelength change appears in the interference light due to the interference unit, and when the wavelength change detecting part detects this wavelength change, the switching signal in the sample can be detected.

The signal interaction part is not particularly limited provided that it can interact with the switching signal, and may be suitably selected according to the purpose, but it is preferred that it can interact with the switching signal by one or both of physical adsorption and chemical adsorption.

The signal interaction part is not particularly limited and may be suitably selected according to the purpose, but it is preferably a signal capturing body which can capture the switching signal. In this case, the signal capturing body is not directly bonded to the substrate, but the signal capturing body is bonded to the rod-shaped material, and the rod-shaped material is bonded to the substrate, so for example if the signal capturing body is an organic substance, instead of bonding this directly to the substrate which is an inorganic substance, it is easier to arrange it on the substrate via a bond with the rod-shaped material which is also an organic substance, and the signal capturing body is also thereby stabilized. Further, even if the substrate surface is not smooth, the signal capturing body can be laid flat, so the light-receiving surface irradiated by the optical irradiation unit can be smoothed, and measurement errors in the wavelength change of the interference light due to the fact that the light-receiving surface is not smooth, can be reduced.

The signal capturing body is not particularly limited provided that it can capture the signal, and may be suitably selected according to the purpose.

The form of the capture is not particularly limited, but may be physical adsorption or chemical adsorption. These may for example be realized by hydrogen bonds, intermolecular forces (van der Waals force), coordination bonds, ionic bonds or covalent bonds.

Specific examples of the signal capturing body are enzymes, coenzymes, enzyme substrates, enzyme inhibitors, clathrate compounds (hereafter, may be referred to as "host compounds" or "hosts"), metals, antibodies, antigens, proteins, microorganisms, viruses, cell debris, metabolic products, nucleic acids, hormones, hormone receptors, lectins, sugars, physiologically active materials and physiologically active material receptors.

When the signal capturing body is an enzyme, the switching signal is for example a coenzyme of this enzyme; when it is a coenzyme, the switching signal is for example an enzyme for which this coenzyme functions as a coenzyme; when it is a clathrate compound, the switching signal is for example a guest compound (included component) of this clathrate compound; when it is an antibody, the switching signal is for example a protein which is an antigen to this antibody; when it is a protein, the switching signal is for example an antibody to which this protein is an antigen; when it is a nucleic acid, the switching signal is for example a complementary nucleic acid to this nucleic acid; when it is a hormone receptor such as tubulin or chitin, it is for example a hormone received by this hormone receptor; when it is a lectin, it is for example a sugar received by this lectin; and when it is a physiologically active material-receiving compound, it is for example a physiologically active material received by this physiologically active material-receptor.

The sample containing the switching signal is not particularly limited and may be suitably selected according to the purpose, but examples are pathogens such as bacteria and viruses, blood, saliva, tissue pathology sections and excreta such as feces and urine. When performing a prenatal diagnosis, the sample may be embryo cells in the amniotic fluid or some dividing egg cells in a test-tube. In these samples, cell destructive treatment may be performed, directly or after concentrating as sediment by centrifuging if necessary, using a combination of for example enzyme treatment, heat treatment, surfactant treatment or ultrasonic treatment.

The clathrate compound is not particularly limited providing that it has molecular recognition ability (host-guest bonding ability), and may be suitably selected according to the purpose, examples being those with a cylindrical (one-dimensional) hollow, those with a stratified (two-dimensional) hollow, or those with a cage-shaped (three-dimensional) hollow.

Examples of clathrate compounds comprising a cylindrical (one-dimensional) hollow are urea, thiourea, deoxycholic acid, dinitrodiphenyl, dioxytriphenylmethane, triphenylmethane, methyl naphthalene, spirochroman, PHTP (perhydrotriphenylene), cellulose, amylose and cyclodextrin (in solution, the hollows are cage-shaped).

Examples of switching signals which can be captured by urea are n-paraffin derivatives.

Examples of switching signals which can be captured by thiourea are branched and cyclic hydrocarbons.

Examples of switching signals which can be captured by deoxycholic acid are paraffins, fatty acids and aromatic compounds.

Examples of switching signals which can be captured by dinitrodiphenyl are diphenyl derivatives.

Examples of switching signals which can be captured by dioxytriphenylmethane are paraffin, n-alkene and squalene.

Examples of switching signals which can be captured by triphenylmethane are paraffins.

Examples of switching signals which can be captured by methylnaphthalene are n-paraffins and branched paraffins up to $C_{16}$.

Examples of switching signals which can be captured by spirochroman are paraffins.

Examples of switching signals which can be captured by PHTP (perhydrotriphenylene) are chloroform, benzene and various polymer substances.

Examples of switching signals which can be captured by cellulose are $H_2O$, paraffins, $CCl_4$, dyes and iodine.

Examples of switching signals which can be captured by amylose are fatty acids and iodine.

Cyclodextrin is a cyclic dextrin generated by decomposition of the amylase in starch, three types, α-cyclodextrin, β-cyclodextrin and γ-cyclodextrin being known. In the present invention, cyclodextrin also includes cyclodextrin derivatives wherein some of these hydroxyl groups are replaced by other functional groups, for example, alkyl groups, allyl groups, alkoxy groups, amide groups and sulfonic acid groups.

Examples of switching signals which can be captured by cyclodextrin are phenol derivatives such as thymol, eugenol, resorcinol, ethylene glycol monophenyl ether and 2-hydroxy-4-methoxy-benzophenone, benzoic acid derivatives such as salicylic acid, methyl parahydroxybenzoate and ethyl p-hydroxybenzoate, and esters thereof, steroids such as cholesterol, vitamins such as ascorbic acid, retinol and tocopherol, hydrocarbons such as limonene, allyl isothiocyanate, sorbic acid, iodine molecules, methyl orange, Congo Red and 2-p-toluidinylnaphthalene-6-sulfonic acid potassium salt (TNS).

The stratified (two-dimensional) clathrate compound may for example be a clay mineral, graphite, smectite, montmorillonite or zeolite.

Examples of switching signals which can be captured by clay minerals are hydrophilic substances and polar compounds.

Examples of switching signals which can be captured by graphite are O, $HSO_4^-$, halogens, halides and alkali metals.

Examples of switching signals which can be captured by montmorillonite are brucine, codeine, o-phenylenediamine, benzidine, piperidine, adenine, guianine and ribosides thereof.

Examples of a switching signal which can be captured by zeolite are $H_2O$ or the like.

The cage-shaped (three-dimensional) clathrate compound may for example be a hydroquinone, gaseous hydrate, tri-o-thymotide, oxyflavane, dicyanoamine nickel, cryptand, calixarene or a crown compound.

Examples of switching signals which can be captured by hydroquinone are HCl, $SO_2$, acetylene and rare gas elements.

Examples of switching signals which can be captured by gaseous hydrates are halogens, rare gas elements and lower hydrocarbons.

Examples of switching signals which can be captured by tri-o-thymotide are cyclohexane, benzene and chloroform.

Examples of switching signals which can be captured by oxyflavane are organic bases.

Examples of switching signals which can be captured by dicyanoamine nickel are benzene and phenol.

Examples of switching signals which can be captured by cryptand are $NH_4^+$ and various metal ions.

Calixarene is a cyclic oligomer wherein phenol units are linked by methylene groups, which can be synthesized under suitable conditions from phenol and formaldehyde, and whereof 4 to 8 nuclides are known. Among these, examples of switching signals which can be captured by p-t-butyl-calixarene (n=4) are chloroform, benzene and toluene. Examples of switching signals which can be captured by p-t-butyl calixarene (n=5) are isopropyl alcohol and acetone. Examples of switching signals which can be captured by p-t-butyl calixarene (n=6) are chloroform and methanol. An example of a switching signal which can be captured by p-t-butyl calixarene (n=7) is chloroform.

Crown compounds include not only crown ethers having oxygen as an electron-donative donor atom, but also, as an analog, large ring compounds having donor atoms such as nitrogen and sulfur as component atoms of the ring system, and also include complex cyclic crown compounds having two or more rings such as cryptand, for example, cyclohexyl-12-crown-4, dibenzo-14-crown-4, t-butylbenzo-15-crown-5, dibenzo-18-crown-6, dicyclohexyl-18-crown-6, 18-crown-6, tribenzo-18-crown-6, tetrabenzo-24-crown-8 and dibenzo-26-crown-6.

Examples of switching signals which can be captured by the crown compound are various metal ions such as alkaline earth metals, e.g., alkali metals such as Li, Na, K, Mg and Ca, $NH_4^+$, alkylammonium ions, guanidium ions and aromatic diazonium ions, this crown compound forming a complex therewith. Examples of other switching signals which can be captured by this crown compound are polar organic compounds containing C—H (acetonitrile, malonitrile and adiponitrile) having a relatively large acidity, N—H (aniline, aminobenzoic acid, amides and sulfamide derivatives) or O—H units (phenol, acetic acid derivatives), this crown compound forming a complex therewith.

The size (diameter) of the hollow of the clathrate compound is not particularly limited and can be suitably selected according to the purpose, but from the viewpoint of manifesting a stable molecular recognition ability (host-guest bonding ability), it is preferably 0.1 nm to 2.0 nm.

Clathrate compounds may also be classified as, for example, monomolecular host compounds, polymolecular host compounds, polymer host compounds and inorganic host compounds.

Examples of monomolecular host compounds are cyclodextrin, crown compounds, cyclophane, azacyclophane, calixarene, cyclotriveratrylene, spherand, cavitand and oligopeptides.

Examples of polymolecular host compounds are urea, thiourea, deoxycholic acid, perhydrotriphenylene and tri-o-thymotide.

Examples of polymer host compounds are cellulose, starch, chitin, chitosan and polyvinyl alcohol.

Examples of inorganic host compounds are intercalation compounds, zeolite and Hofmann type complexes.

The antibody is not particularly limited provided that it undergoes an antigen-antibody reaction with a specific antigen, but it may be a polyclonal antibody or monoclonal antibody, and further contain IgG, IgM, IgE, Fab', Fab, F(ab')$_2$ of IgG, or avidin.

The antigen is not particularly limited and can be suitably selected according to the type of antibody, for example plasma proteins, tumor markers, apoproteins, virus antigens, autoantibodies, coagulation/fibrinolysis factor, hormones, drugs in blood, HLA antigens and biotin.

Examples of plasma proteins are immunoglobulin (IgG, IgA, IgM, IgD, IgE), complementary components (C3, C4, C5, C1q), CRP, $\alpha_1$-antitrypsin, $\alpha_1$-microglobulin, $\beta_2$-microglobulin, haptoglobin, transferrin, ceruloplasmin and ferritin.

Examples of tumor markers are α-fetoprotein (AFP), carcinoembryonic antigen (CEA), CA 19-9, CA125 and CA 15-3, SCC antigen, prostate gland acid phosphatase (PAP), PIVKA-II, γ-seminoprotein, TPA, Elastase I, nerve specific enolase (NSE) and immunosuppression acidic protein (IAP).

Examples of apoproteins are apo A-I, apo A-II, apo B, apo C-II, apo C-III and apo E.

Examples of virus antigens are hepatitis B virus (HBV)-related antigen, hepatitis C virus (HVC)-related antigen, HTLV-I, HIV, rabies virus, influenza virus and rubella virus.

Examples of HCV-related antigens are HCVc100-3 recombinant antigen, pHCV-31 recombinant antigen and pHCV-34 recombinant antigen, and mixtures thereof may be used. Examples of HIV-related antigens are virus surface antigen, e.g., HIV-I env.gp41 recombinant antigen, HIV-I env.gp120 recombinant antigen, HIV-I gag.p24 recombinant antigen and HIV-II env.p36 recombinant antigen.

Other infections apart from viruses are MRSA, ASO, toxoplasma, mycoplasma and STD.

Examples of autoantibodies are anti-microzome antibody, anti-siloglobulin antibody, antinuclear antibody, rheumatism factor, anti-mitochondrion antibody and myelin antibody.

Examples of coagulation/fibrinolysis factor are fibrinogen, fibrin cleavage product (FDP), plasminogen, $\alpha_2$-plasmin inhibitor, Antithrombin III, β-thromboglobulin, Factor VIII, Protein C and Protein S.

Examples of hormones are pituitary hormones (LH, FSH, GH, ACTH, TSH, prolactin), thyroid hormones ($T_3$, $T_4$, siloglobulin), calcitonin, parathyroid hormone (PTH), adenocoriticotropic hormones (aldosterone, cortisol), gonad hormone (hCG, estrogen, testosterone, hPL), and pancreatic and gastrointestinal hormones (insulin, C-peptide, glucagon, gastrin). Other examples are (renin, Angiotensin I and II, enkephalin and erythropoietin).

Examples of drugs in blood are antiepileptics such as carbamazepine, primidone and valproic acid, circulatory organ disease drugs such as digoxin, quinidine, digitoxin and theophylline, and antibiotics such as gentamycin, kanamycin and streptomycin.

These proteins may be low molecular weight molecules (about 6000 to 13000) which show high affinity with heavy metals, in particular zinc, cadmium, copper and mercury. The proteins are present in the liver, kidney and other organs of the animal, and have recently been shown to be present also in microorganisms. They have a high cysteine content, and show an aminoacid distribution containing almost no aromatic residues. They are important substances which have detoxication functions, such as eliminating cadmium and mercury from the body, and also participate in the storage and distribution of trace metals indispensable to the living body such as zinc and copper.

Examples of heavy metals are alkyl mercury compounds (R—Hg), mercury or its compounds (Hg), cadmium or its compounds (Cd), lead or its compounds (Pb), hexavalent chromium ($Cr_6^+$), copper or its compounds (Cu), zinc or its compounds (Zn), cyan, arsenic, selenium, manganese, nickel, iron, zinc, selenium, and tin.

The method of bonding the signal capturing body to the rod-shaped organic molecules (rod-shaped object) is not particularly limited and can be suitably selected according to the type of signal capturing body and rod-shaped organic molecules. Examples are methods known in the art, i.e., the method of using covalent bonds such as ester bonds or amide bonds, the method wherein a protein is labeled with avidin, and bonded to a biotin-modified capturing structure, and the method wherein a protein is labeled with streptavidin, and bonded to a biotin-modified capturing structure.

In the optical switch according to the present invention, due to the use of these methods, any desired signal capturing body can easily be bonded to the rod-shaped organic molecules, so unlike the case where this signal capturing body is directly bonded to the substrate, the signal capturing body or switching signal can be freely selected over a wide range, the optical switch can be used for a wide range of applications regardless of the purpose or type of switching signal, and as the surface of the signal capturing body can be kept smooth, wavelength variation unevenness of the interference light and measurement errors are small, so detection can be performed with high sensitivity.

Examples of using covalent bonds are the peptide method, diazo method, alkylation, cyanogen bromide activation, bonding by crosslinking agent, the fixing method using the Ugi reaction, the fixing method using a thiol disulfide exchange reaction, the Schiff base-forming method, the chelate bond method, the tosyl chloride method and biochemical-specific bonding, but to obtain more stable bonds such as covalent bonds, methods using the reaction of a thiol group with a maleimide group, the reaction of a pyridyl disulfide group with a thio group and the reaction of an amino group with an aldehyde group are preferred, and the method of using a chemical binder or crosslinking agent is more preferred.

Examples of such chemical binders and crosslinking agents are carbodiimides, isocyanates, diazo compounds, benzoquinones, aldehydes, periodic acids, maleimido compounds and pyrydyl disulfide compounds. Specific examples thereof are glutaraldehyde, hexamethylene diisocyanate, hexamethylene diisothiocyanate, N,N'-polymethylene bis-iodine acetamide, N,N'-ethylene bis-maleimide, ethylene glycol bis-succinimidyl succinate, bis-diazobenzidine, 1-ethyl-3-(3-dimethyl amino propyl) carbodiimide, succinimidyl 3-(2-pyridyldithio)propionate (SPDP), N-succinimidyl 4-(N-maleimido methyl)cyclohexane-1-carboxylate (SMCC), N-sulfosuccinimidyl 4-(N-maleimido methyl)cyclohexane-1-carboxylate, N-succinimidyl (4-iodine acetyl) aminobenzoate, N-succinimidyl 4-(1-maleimidophenyl) butyrate, iminothioran, S-acetyl mercaptosuccinic acid anhydride, methyl-3-(4'-dithiopyrydyl)propionimidate, methyl-4-mercaptobutylylimidate, methyl-3-mercapto propionimidate and N-succinimidyl-S-acetyl mercaptoacetate.

In the present invention, the optical interference unit may radiate the interference light as transmitted light, or it may radiate the interference light as reflected light. In the former case, the optical switch can be made a reflecting type apparatus, whereas in the latter case, the optical switch can be made a transmitting type apparatus.

<Switching Unit>

The switching unit 40 is not particularly limited, and may be selected according to the purpose, provided that it is arranged in the path of the interference light, can detect the wavelength change of the interference light which is radiated by the optical interference unit, and has a function which can perform one of activating and deactivating a circuit. Preferable examples include one that comprises a wavelength change detecting part 40a which is arranged in the path of the interference light, and which detects the wavelength change of the interference light radiated from the optical interference unit; and a circuit operation controlling part 40b which can perform one of activating and deactivating a circuit when the wavelength change detecting part detects the wavelength change of the interference light (FIGS. 12A and 12B).

Wavelength Change Detecting Part

The wavelength change detecting part is not particularly limited provided that it is arranged in the path of the interference light and detects the wavelength change of the interference light radiated from the optical interference unit, and may be suitably selected according to the purpose. Preferable examples include, (1) one that only allows light having a specific wavelength to pass through and that can detect this light having the specific wavelength; and (2) one that measures a spectrum before wavelength change of the interference light and a spectrum after wavelength change of the interference light so as to determine and measure the differential spectrum of the two spectra.

Among these, in the case of the (1), it is possible to detect easily, quickly, and with high sensitivity by prohibiting transmittance of interference light before the switching signal interacts with the optical interference unit, but by allowing transmittance of interference light having a specific wavelength after the switching signal interacts with the optical interference unit and changes the wavelength of the interference light to the specific wavelength, or alternatively, by allowing transmittance of interference light having specific wavelength before the switching signal interacts with the optical interference unit, but by prohibiting transmittance of interference light after the switching signal interacts with the optical interference unit and changes the wavelength of the interference light. In this way, even if it is very difficult to detect a slight change, i.e., if there is only a slight wavelength change (wavelength shift) by simply measuring the ordinary spectral curve, this can be easily and reliably detected. As the wavelength change detecting part detects the transmission of this interference light, the wavelength change of the interference light can be detected, and the interaction of the switching signal with the optical interference unit, i.e., the presence of this switching signal in the sample, can be detected easily, rapidly and with high sensitivity, and this in turn provides an excellent switching performance.

Alternatively, in the case of the (2), the spectral difference before and after the wavelength of the interference light has changed, i.e., the differential spectrum, is measured by the wavelength change detecting part, so if a slight change is very difficult to measure by measuring only the ordinary spectral curve, i.e., when there is only a very small wavelength change (wavelength shift), this can be detected with ease and reliability, the wavelength change can be transformed into a spectral intensity, and this can be amplified as desired. As a result, even a very small wavelength change can be detected as an amplified spectral intensity, and can be detected with high sensitivity by a simple, rapid and highly sensitive detection, and this in turn provides an excellent circuit switching performance.

A specific example of (1) is a combination of an interference filter 40a' with an optical detection sensor 40a" which can detect transmitted light which has passed through the interference filter as shown in FIGS. 12A and 12B. In this case, it is possible to detect existence of a switching signal by setting the interference filter 40a' so that it prohibits transmittance of interference light before the switching signal interacts with the optical interference unit 20, but allows transmittance of interference light having a specific wavelength after the switching signal interacts with the optical interference unit 20 and changes the wavelength of the interference light to the specific wavelength, or alternatively, so that it allows transmittance of interference light having specific wavelength before the switching signal interacts with the optical interference unit 20, but prohibits transmittance of interference light after the switching signal interacts with the optical interference unit 20 and changes the wavelength of the interference light. In this way, even if it is very difficult to detect a slight change, i.e., if there is only a slight wavelength change (wavelength shift) by simply measuring the ordinary spectral curve, this can be easily and reliably detected. As the optical detection sensor 40a" detects the transmission of this interference light through the interference filter 40a', the wavelength change of the interference light is detected, and the interaction of the switching signal with the optical interference unit, i.e., the presence of this switching signal in the sample, can be detected. As a result, even if there is only a very slight wavelength change, the optical detection sensor 40a" can detect the transmitted interference light, and with high sensitivity, and this in turn provides an excellent circuit switching performance.

The interference filter is not particularly limited and may be suitably selected according to the purpose, and commercial products may also be used.

The interference filter interferes only with incident light of a specific wavelength, and transmits incident light of wavelengths other than the specific wavelength.

The optical detection sensor is not particularly limited and may be suitably selected according to the purpose, examples being a CdS cell, photodiode, photoelectric tube, pyroelectric sensor, CCD sensor or PSD sensor.

Specific examples of (2) are spectrophotometers known in the art.

In the optical switch according to the present invention, the optical irradiation unit irradiates light. The optical interference unit interferes with the light irradiated from the optical irradiation unit, and radiates as an interference light. The optical interference unit can interact with the switching signal, and after interacting with the switching signal, the wavelength of the interference light is changed. The wavelength change detecting part detects the wavelength change of the interference light radiated by the optical interference unit. As a result, due to the wavelength change of the interference light detected by the wavelength change detecting part, the interaction of the switching signal with the optical interference unit, i.e., the presence of the switching signal in the sample, can be detected.

Circuit Operation Controlling Part

The circuit operation controlling part is not particularly limited and may be selected according to the purpose, provided that it has a function which performs one of activating and deactivating a circuit when the wavelength change detecting part detects the wavelength change of the interference light. Preferable examples thereof include computer and the like.

The circuit is not particularly limited and may be selected according to the purpose. Preferable examples thereof include electric circuits and various apparatuses such as safety apparatuses which include such electric circuits.

The optical switch of the present invention may be used in many fields, and may be used preferably as a switch which detects various switching signals such as pathogens, physiological substances, and toxic substances efficiently, reliably, and easily, and which can operate a safety apparatus or the like when detecting a switching signal.

(Safety Apparatus)

The safety apparatus of the present invention activates a hazard evasive apparatus using the optical switch of the present invention. Specifically, it comprises an optical irradiation unit, an optical interference unit, a wavelength change detecting unit, a hazard evasive apparatus activating unit, and other units selected appropriately upon necessity.

For the optical irradiation unit, ones that are the same as those for the optical switch may be used. For the optical interference unit, ones that are the same as those for the optical switch may be used. Preferable examples include ones that comprise at least a film-like material having rod-shaped materials arranged therein.

The film-like material may be suitably selected from the same ones for the optical switch, and among them, ones having rod-shaped materials arranged therein and being formed on a substrate are preferable. In this case, as the film-like material is provided on the substrate, the structural stability of this film-like material and surface smoothness are excellent, detection errors can be reduced, and the malfunction of the safety apparatus can be prevented.

The rod-shaped material preferably comprises a signal interaction part which can interact with the hazard signal. In this case, due to the interaction of this signal interaction part of the rod-shaped material with the hazard signal, a wavelength change appears in the interference light due to the interference unit, and when the wavelength change detecting unit detects this wavelength change, the hazard signal in the sample can be detected.

The signal interaction part is not particularly limited provided that it can interact with the hazard signal, and may be suitably selected according to the purpose, but it is preferred that it can interact with the hazard signal by one or both of physical adsorption and chemical adsorption.

The signal interaction part is not particularly limited and may be suitably selected according to the purpose, but it is preferably a hazard signal capturing body which can capture the hazard signal. In this case, the hazard signal capturing body is not directly bonded to the substrate, but the hazard signal capturing body is bonded to the rod-shaped material, and the rod-shaped material is bonded to the substrate, so for example if the hazard signal capturing body is an organic substance, instead of bonding this directly to the substrate which is an inorganic substance, it is easier to arrange it on the substrate via a bond with the rod-shaped material which is also an organic substance, and the hazard signal capturing body is also thereby stabilized. Further, even if the substrate surface is not smooth, the hazard signal capturing body can be laid flat, so the light-receiving surface irradiated by the optical irradiation unit can be smoothed, and detection errors in the wavelength change of the interference light due to the fact that the light-receiving surface is not smooth, can be reduced.

The hazard signal capturing body is not particularly limited provided that it can capture the hazard signal, and may be suitably selected according to the purpose.

The form of the capture is not particularly limited, but may be physical adsorption or chemical adsorption. These may for example be realized by hydrogen bonds, intermolecular forces (van der Waals force), coordination bonds, ionic bonds or covalent bonds.

Specific examples of the hazard signal capturing body are enzymes, coenzymes, enzyme substrates, enzyme inhibitors, clathrate compounds (hereafter, may be referred to as "host compounds" or "hosts"), metals, antibodies, antigens, proteins, microorganisms, viruses, cell debris, metabolic products, nucleic acids, hormones, hormone receptors, lectins, sugars, physiologically active materials and physiologically active material receptors.

When the hazard signal capturing body is an enzyme, the hazard signal is for example a coenzyme of this enzyme; when it is a coenzyme, the hazard signal is for example an enzyme for which this coenzyme functions as a coenzyme; when it is a clathrate compound, the hazard signal is for example a guest compound (included component) of this clathrate compound; when it is an antibody, the hazard signal is for example a protein which is an antigen to this antibody; when it is a protein, the hazard signal is for example an antibody to which this protein is an antigen; when it is a nucleic acid, the hazard signal is for example a complementary nucleic acid to this nucleic acid; when it is a hormone receptor such as tubulin or chitin, it is for example a hormone received by this hormone receptor; when it is a lectin, it is for example a sugar received by this lectin; and when it is a physiologically active material-receiving compound, it is for example a physiologically active material received by this physiologically active material-receptor. For the clathrate compound, the ones that are the same as those for the optical switch may be used.

The sample containing the hazard signal is not particularly limited and may be suitably selected according to the purpose, but examples are pathogens such as bacteria and viruses, blood, saliva, tissue pathology sections and excreta such as feces and urine. When performing a prenatal diagnosis, the sample may be embryo cells in the amniotic fluid or some dividing egg cells in a test-tube. In these samples, cell destructive treatment may be performed, directly or after concentrating as sediment by centrifuging if necessary, using a combination of for example enzyme treatment, heat treatment, surfactant treatment or ultrasonic treatment.

The wavelength change detecting unit is not particularly limited provided that it is arranged in the path of the interference light and detects the wavelength change of the interference light radiated from the optical interference unit, and may be suitably selected according to the purpose. Preferable examples include, (1) one that only allows light having a specific wavelength to pass through and that can detect this light having the specific wavelength; and (2) one that measures a spectrum before wavelength change of the interference light and a spectrum after wavelength change of the interference light so as to determine and measure the differential spectrum of the two spectra.

Among these, in the case of the (1), it is possible to detect easily, quickly, and with high sensitivity by prohibiting transmittance of interference light before the hazard signal interacts with the optical interference unit, but by allowing transmittance of interference light having a specific wavelength after the hazard signal interacts with the optical interference unit and changes the wavelength of the interference light to the specific wavelength, or alternatively, by allowing transmittance of interference light having specific wavelength before the hazard signal interacts with the optical interference unit, but by prohibiting transmittance of interference light after the hazard signal interacts with the optical interference unit and changes the wavelength of the interference light. In this way, even if it is very difficult to detect a slight change, i.e., if there is only a slight wavelength change (wavelength shift) by simply measuring the ordinary spectral curve, this can be easily and reliably detected. As the wavelength change detecting unit detects the transmission of this interference light, the wavelength change of the interference light can be detected, and the interaction of the hazard signal with the optical interference unit, i.e., the presence of this hazard signal in the sample, can be detected easily, rapidly and with high sensitivity, and this in turn provides excellent hazard evading performance and safety.

Alternatively, in the case of the (2), the spectral difference before and after the wavelength of the interference light has changed, i.e., the differential spectrum, is measured by the wavelength change detecting unit, so if a slight change is very difficult to measure by measuring only the ordinary spectral curve, i.e., when there is only a very small wavelength change (wavelength shift), this can be detected with ease and reliability, the wavelength change can be transformed into a spectral intensity, and this can be amplified as desired. As a result, even a very small wavelength change can be detected as an amplified spectral intensity, and can be detected with high sensitivity by a simple, rapid and highly sensitive detection, and this in turn provides excellent hazard evading performance and safety.

A specific example of (1) is a combination of an interference filter with an optical detection sensor which can detect transmitted light which has passed through the interference filter. In this case, it is possible to detect existence of a hazard signal by setting the interference filter so that it prohibits transmittance of interference light before the hazard signal interacts with the optical interference unit, but allows transmittance of interference light having a specific wavelength after the hazard signal interacts with the optical interference unit and changes the wavelength of the interference light to the specific wavelength, or alternatively, so that it allows transmittance of interference light having specific wavelength before the hazard signal interacts with the optical interference unit, but prohibits transmittance of interference light after the hazard signal interacts with the optical interference unit and changes the wavelength of the interference light. In this way, even if it is very difficult to detect a slight change, i.e., if there is only a slight wavelength change (wavelength shift) by simply measuring the ordinary spectral curve, this can be easily and reliably detected. As the optical detection sensor detects the transmission of this interference light through the interference filter, the wavelength change of the interference light is detected, and the interaction of the hazard signal with the optical interference unit, i.e., the presence of this hazard signal in the sample, can be detected. As a result, even if there is only a very slight wavelength change, the optical detection sensor can detect the transmitted interference light, and with high sensitivity, and this in turn provides excellent hazard evading performance and safety.

The interference filter is not particularly limited and may be suitably selected according to the purpose, and commercial products may also be used.

The interference filter interferes only with incident light of a specific wavelength, and transmits incident light of wavelengths other than the specific wavelength.

The optical detection sensor is not particularly limited and may be suitably selected according to the purpose, examples being a CdS cell, photodiode, photoelectric tube, pyroelectric sensor, CCD sensor or PSD sensor.

Specific examples of (2) are spectrophotometers known in the art.

In the safety apparatus according to the present invention, the optical irradiation unit irradiates light. The optical interference unit interferes with the light irradiated from the optical irradiation unit, and radiates as an interference light. The optical interference unit can interact with the hazard signal, and after interacting with the hazard signal, the wavelength of the interference light is changed. The wavelength change detecting unit detects the wavelength change of the interference light radiated by the optical interference unit. As a result, due to the wavelength change of the interference light detected by the wavelength change detecting unit, the interaction of the hazard signal with the optical interference unit, i.e., the presence of the hazard signal in the sample, can be detected.

Hazard Evasive Apparatus Activating Unit

The hazard evasive apparatus activating unit is not particularly limited and may be selected according to the purpose, provided that it has a function which activates a hazard evasive apparatus when the wavelength change detecting unit detects the wavelength change of the interference light. Preferable examples include a gas emitting device, a smoke emitting device, a heat insulating device, a cooling device, a heating device, a light blocking device, a light irradiating device, a waste water blocking device, and a combination of these with a computer.

The hazard evasive apparatus is not particularly limited and may be selected according to the purpose. Examples include a gas emitting device, a smoke emitting device, a heat insulating device, a cooling device, a heating device, a light blocking device, a light irradiating device, and a waste water blocking device.

The safety apparatus of the present invention may be used in various fields, and may be suitably used as a safety apparatus which can avoid a hazard by activating a hazard evasive apparatus upon detecting, as a hazard signal, existence of a substance of various kinds such as pathogens, physiological substances, and toxic substances.

Hereafter, the present invention will be described by means of examples, but it will be understood that the invention should not be construed as being limited thereby.

Example 1

First, a monomolecular film of an α-helix polypeptide was formed on a substrate as the rod-shaped organic molecule, a laminated film (film-like material) was formed by laminating the same monomolecular film on this monomolecular film, and the relation between the number of laminated layers and the structural coloration was examined.

As the α-helix polypeptide, poly(n-hexyl L-glutamate) (hereafter referred to as "PHeLG") was used comprising a monomer unit wherein the hydrogen atom of the carboxyl group of glutamic acid was replaced by a n-hexyl group. This PHeLG was obtained by a polymerization reaction of L-glutamic acid-γ methyl ester using benzylamine as polymerization initiator, and the polymerization degree as measured by $^1$H-NMR was 114. The substrate was a silicone substrate (Shin-Etsu Chemical Co., Ltd.) subjected to a surface treatment by octadecyl trimethoxysilane (Tokyo Chemical Industries). The monomolecular film was formed using a LB film-forming apparatus Japan Laser & Electronics Laboratory, NL-LB400 NK-MWC). In addition, in PHeLG, the pitch of the spiral of the α-helix was 0.15 nm per amino acid residue, and the diameter of the α-helix was 1.5 nm.

For a laminated film (film-like material) comprising a laminate of 120 of these monomolecular film layers, when the FT-IR spectrum was measured, four peaks were obtained. One is a peak at 1738 cm$^{-1}$ due to the C=O group of the side chain. Another is a strong peak at 1656 cm$^{-1}$ due to an amide group I in the α-helix structure. Another is a small, weak peak at 1626 cm$^{-1}$ due to an amide group I in the β-structure. The last one is a peak at 1551 cm$^{-1}$ due to an amide group II in the α-helix structure. From the measurement results of this FT-IR spectrum, it was confirmed that the above-mentioned PHeLG molecule maintains an α-helical structure in the monomolecular film.

Regarding the monomolecular film due to PHeLG, as the thickness when there were 20 monomolecular film layers due to this PHeLG was 32 nm, the thickness per layer was computed to be 1.6 nm.

Figure 6:
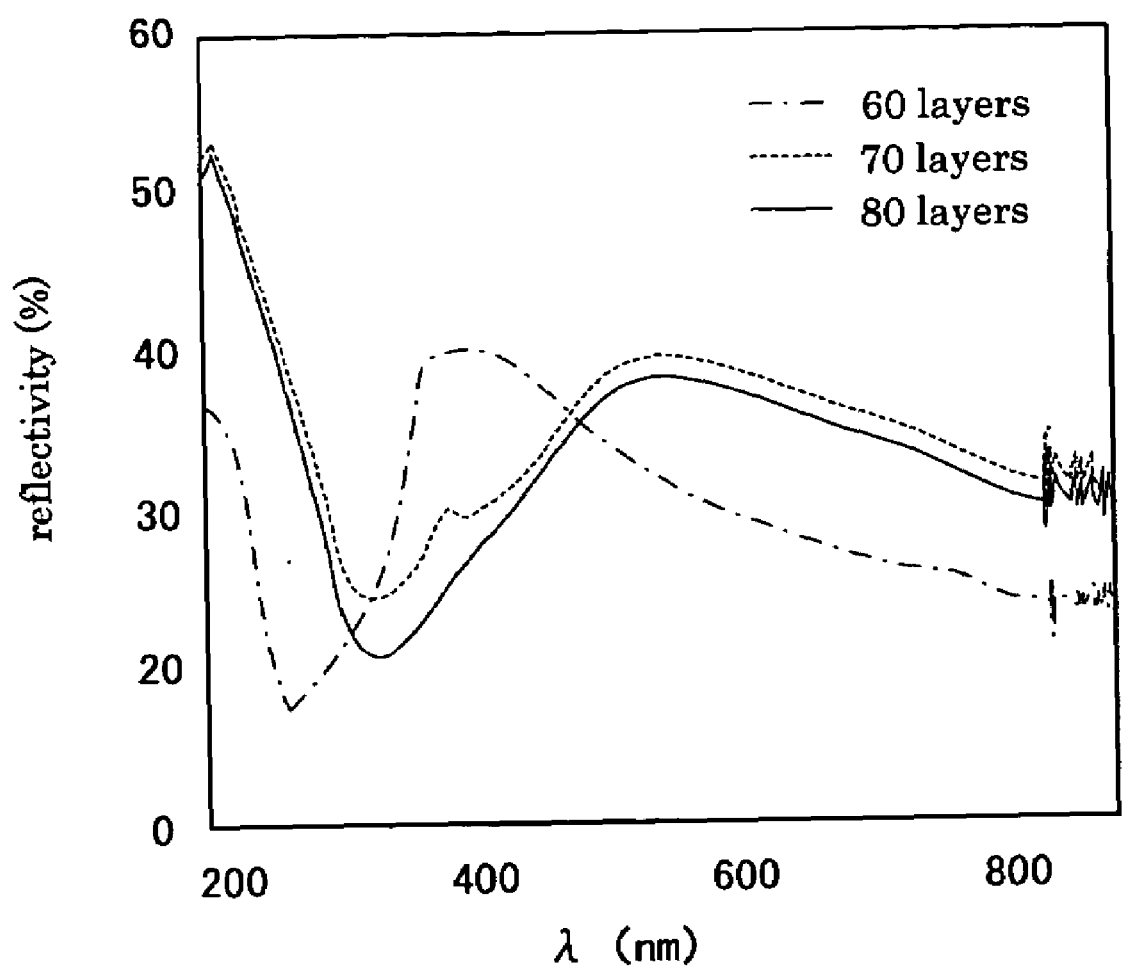
FIG. 6 is a graph showing the relation of the wavelength of structural color due to a laminated film (60 layers, 70 layers, 80 layers) of monomolecular films of rod-shaped organic molecules, and the thickness of this laminated film.

Next, when the relation between the number of laminated layers and structural coloration in the laminated film (film-like material) due to this monomolecular film was examined, it was found that when this laminated film contained 60 layers, 70 layers and 80 layers of these monomolecular films, the visible light reflection spectra shown in FIG. 6 were obtained. Also, a laminated film (film-like material) containing 40 to 50 layers of these monomolecular films showed a brown coloration, a laminated film (film-like material) containing 60 to 70 layers of these monomolecular films showed a dark blue (deep blue) coloration, a laminated film (film-like material) containing 80 to 100 layers of these monomolecular films showed a light blue (thin blue) coloration, a laminated film (film-like material) containing nearly 120 layers of these monomolecular films showed a yellow coloration, and a laminated film (film-like material) containing up to 160 layers of these monomolecular films showed a purplish red coloration.

Figure 7:
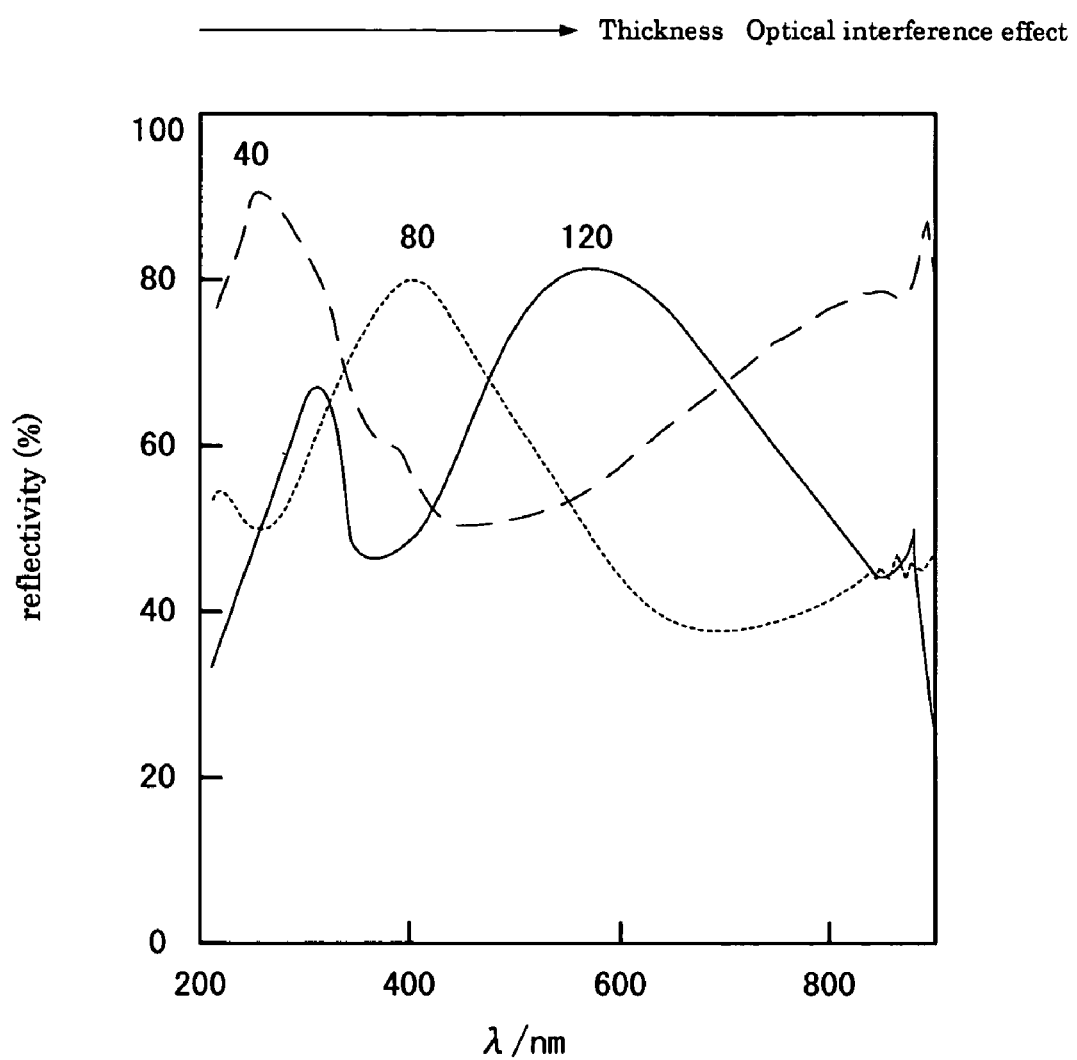
FIG. 7 is a graph showing the relation of the wavelength of structural color due to a laminated film (40 layers, 80 layers, 120 layers) of monomolecular films of rod-shaped organic molecules, and the thickness of this laminated film.

FIG. 7 shows the visible light reflection spectra for when the laminated film (film-like material) contained 40 layers of these monomolecular films, when the laminated film (film-like material) contained 80 layers, and when the laminated film (film-like material) contained 120 layers of these monomolecular films. The laminated film (film-like material) containing 80 layers showed a maximum reflectance (%) peak at 418 nm, and had a blue color. The laminated film (film-like material) containing 40 layers showed a minimum reflectance (%) at 456 nm, and had a brown (dark orange) color which is the complementary color to blue. On the other hand, the laminated film (film-like material) containing 120 layers showed a maximum reflectance (%) peak at 619 nm, a minimum reflectance (%) at 409 nm, and had a yellow color due to the light at 619 nm emphasized by the enfeebled light of wavelength 409 nm.

The wavelength (λ) of the visible light reflection spectrum is affected by the incidence angle (α) of the light on the laminated film (film-like material) due to the monomolecular film. The conditions under which this wavelength (λ) is emphasized are shown in the following formula (1), and the conditions under which this wavelength (λ) is enfeebled are as shown in the following formula (2):

$$\lambda = \frac{2tl}{m}\sqrt{n^2 - \sin^2\alpha} \quad (1)$$

$$\lambda = \frac{4tl}{2m-1}\sqrt{n^2 - \sin^2\alpha} \quad (2)$$

In the above-mentioned formula (1) and the above-mentioned formula (2), λ is the wavelength (nm) of the interference light, α is the incidence angle (°) of the light on the monomolecular film or the laminated film, t is the thickness (nm) of a monomolecular film, "l" is the number of monomolecular films, "n" is the refractive index of a monomolecular film, and "m" is an integer equal to 1 or more.

Figure 8:
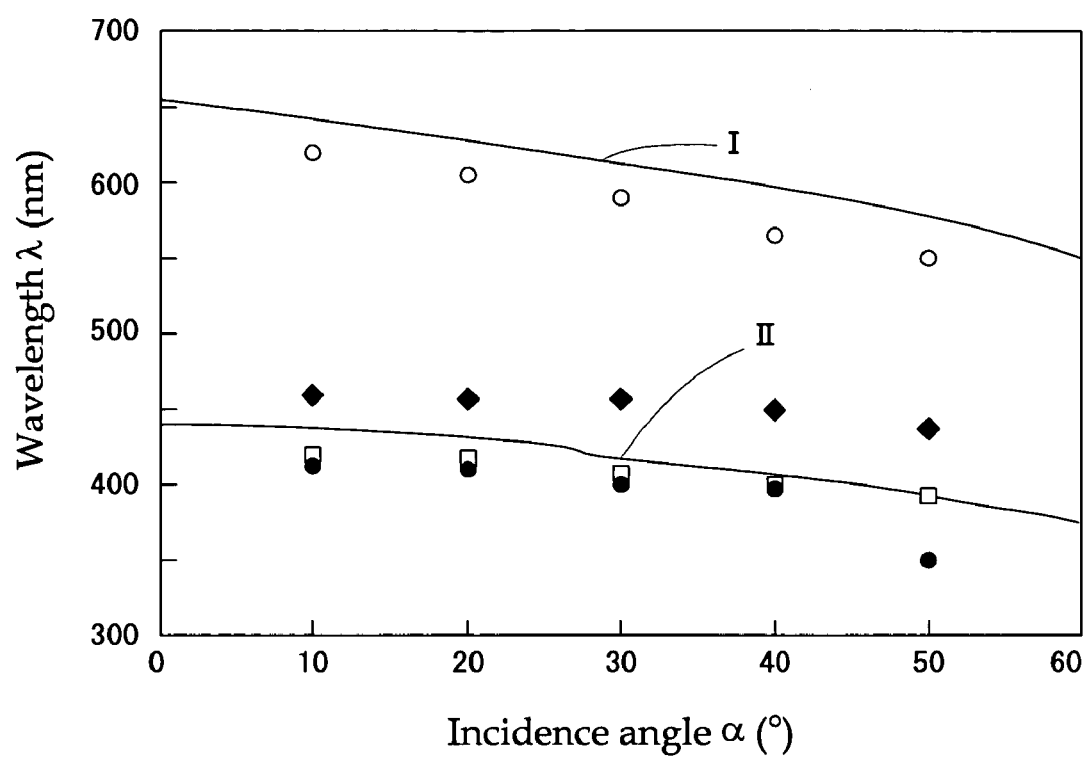
FIG. 8 is a graph showing the relation of a light incidence angle α(°) to the laminated film (40 layers, 80 layers, 120 layers) of monomolecular films of rod-shaped organic molecules, and a reflection wavelength γ(nm).

When the relation between the wavelengths (λ) of minimum and maximum intensity of the visible light reflection spectrums and the incidence angle (α) of the light on the laminated film (film-like material) of the monomolecular film was examined, as shown in FIG. 8, it was found that the measured values of the wavelength (λ) of the 5 reflection spectra for 5 incidence angles, effectively coincided with the wavelength (λs) computed by the formulae (1) and (2).

In FIG. 8, filled squares represent the wavelengths of minimum intensity in spectrums of the laminated film comprising 40 layers, open squares represent the wavelengths of maximum intensity in spectrums of the laminated film comprising 80 layers, open circles represent the wavelengths of maximum intensity in spectrums of the laminated film comprising 120 layers, and filled circles represent the wavelengths of minimum intensity in spectrums of the laminated film comprising 120 layers. The Line I was computed from Equation (1) for the conditions "l"=120 and "m"=1, and the Line II was computed from Equation (1) for the conditions "l"=80 and "m"=1, from Equation (2) for the conditions "l"=40 and "m"=1, or from Equation (2) for the conditions "l"=120 and "m" =2, respectively for the conditions "t"=1.7 (nm) and "n"=1.6 (the lines for these three calculation results effectively mutually overlap).

In this way, it was found that when light is irradiated to the film-like material having a specific thickness provided on the substrate, the interference light due to the film-like material has a wavelength in the visible spectrum and can be identified as an interference color.

Preparation of Optical Interference Unit

Next, as the substrate on which the film-like material is arranged, a pre-colored substrate having an oxide film was manufactured as follows. An oxide film ($SiO_2$ film) 50a was formed on the surface of a silicon substrate by heat-treating the silicon substrate (Shin-Etsu Chemicals) at approximately 1000° C. for 3 hours. For this pre-colored substrate, its interference light (peak top is about 508 nm (thin line in FIG. 18)) is green, and it had a green color. The surface area of the silicon substrate is $3 \times 10^{14}$ $nm^2$ (15 mm×20 mm).

On the other hand, according to the following synthesis scheme, poly benzyl-L-glutamate having biotin at the end ($PBLG_{21}$-bio) was synthesized as the α-helix polypeptide which is the rod-shaped organic molecule. Specifically, poly benzyl-L-glutamate ($PBLG_{21}$-bio) having a polymerization degree of 21 was synthesized by carrying out a polymerization of the benzyl-L-glutamate derivative (BLG-NCA) synthesized by the synthesis scheme shown in formula (3), using the biotin derivative shown in formula (4) as a polymerization initiator.

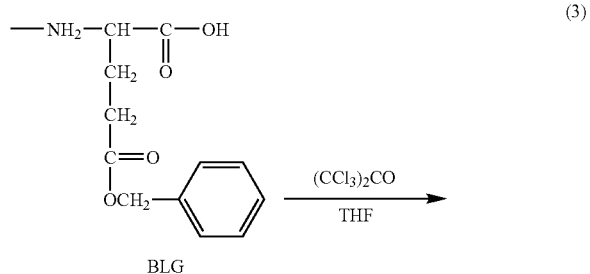

BLG (3)

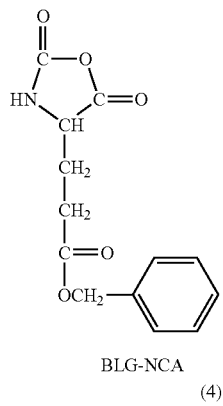

BLG-NCA (4)

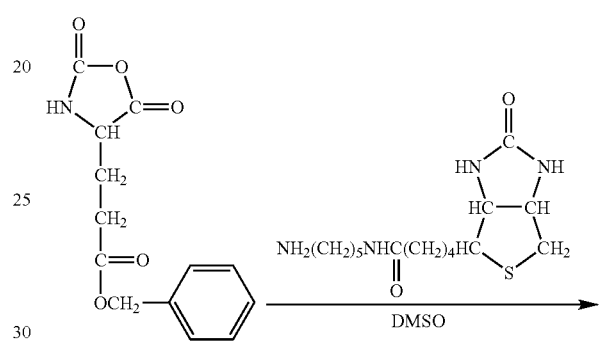

BLG-NCA

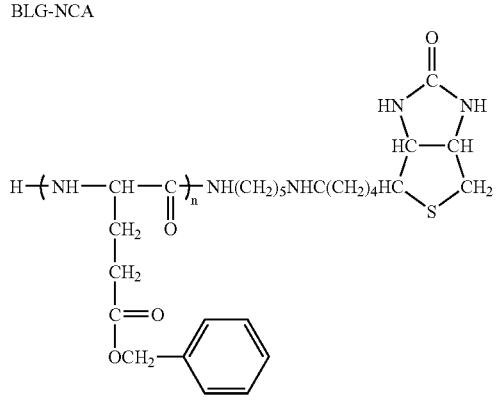

$PBLG_n$-bio (n = 21)

When the refractive index of this polybenzyl-L-glutamate ($PBLG_{21}$-bio) was measured using an Abbe's refractometer (Atago Co., Ltd.), it was about 1.5.

Ten layers of this synthetic polybenzyl-L-glutamate ($PBLG_{21}$-bio) were laminated on a substrate 50 by the LB method at a cumulative pressure of 9.5 mN/m (Shown in FIG. 9, laminated at a cumulative pressure on the vertical axis of 9.5 mN/m). Specifically, a lamination layer film 20 (film thickness approx. 13.25 nm) comprising ten layers of the monomolecular (film thickness approx. 1.33 nm) having this polybenzyl-L-glutamate ($PBLG_{21}$-bio) as the rod-shaped organic molecule 10, was formed (Shown in FIG. 10, where the lamination film does not show ten layers to simplify the illustration). The optical interference unit thus obtained gives an interference light color (interference color, peak top approx. 545 nm (dotted line of FIG. 18)) which is yellowish, and it had a yellowish color. The conditions under which this interference light is emphasized or enfeebled are as shown in the formulae of FIG. 11 wherein symbols and characters are as indicated in the upper drawing. FIG. 12A and FIG. 12B show the measurement of the interference light (interference color) in the pre-colored substrate (wherein the film-like material is not provided) (FIG. 12A), and the measurement of the interference light (interference color) in the optical interference unit (FIG. 12B).

Interaction Between Optical Interference Unit and Switching Signal

The optical interference unit, i.e., the laminated film formed on the pre-colored substrate, was immersed in an aqueous solution ($1.1 \times 10^{-7}$ M) of avidin as the switching signal, and biotin as the signal capturing body in the optical interference unit was made to interact (adsorption reaction) with avidin which was the switching signal. The cross-sectional surface area of avidin was a little less than about 30 nm$^2$ (3 nm×3 nm×3.14). FIG. 13 is a schematic diagram of the interaction (adsorption reaction) of biotin and avidin in this example, FIG. 14 is a schematic diagram showing the state where the optical interference unit is immersed in the aqueous solution of avidin, and FIG. 15 is a schematic diagram showing the interaction (adsorption reaction) of biotin in the optical detection unit with avidin in the aqueous solution of avidin. Subsequently, this optical detection unit was washed with pure water.

Wavelength Change Detection

As the optical irradiation unit, a spectrophotometer (Jasco Corp., V560) was used as a light source. Light (xenon lamp light) was irradiated by this optical irradiation unit so that the incidence angle on the optical interference unit was 10°. The reason why the incidence angle was selected to be 10°, was that the incidence angle was selected from measurement data of the incidence angle dependence of the interference light in FIGS. 16 and 17.

The spectrophotometer (Jasco Corp., V560) was disposed as a light-receiving unit in the path of the reflected light (interference light) due to the optical interference unit from the light irradiated by the optical irradiation unit to measure the spectral wavelengths of this reflected light (interference light), the peak top was 565 nm (bold line in FIG. 18), and a peak shift of approximately 20 nm was observed compared to the situation before the interaction between the optical interference unit and switching signal. If calculations are performed assuming a refractive index of 1.5, this 20 nm corresponds to a film thickness variation of approximately 7.16 nm. This is confirmed to be due to adsorption of avidin having a diameter of approximately 6 nm on the surface of the optical interference unit.

<Calculation of Avidin Adsorption Amount>

The number of avidin adsorptions on the substrate can be computed from cross-sectional surface area of substrate/cross-sectional surface area of one avidin molecule, and was found to be $3 \times 10^{14}/3 \times 10^{1} = 1 \times 10^{13}$ parts. Next, the number of absorption moles of avidin on this substrate can be computed from this number of adsorptions/Avogadro's number, and was found to be $1 \times 10^{13}/6 \times 10^{23} = 17 \times 10^{-12}$M=17 pM.

Therefore, it was found that the avidin adsorption amount for a wavelength shift in the interference light of 20 nm is 17 pM.

Further, when the surface area of the substrate was approximately 5 mm$^2$, the wavelength shift (peak top shift) of the interference light for an avidin adsorption amount of 1.4 pM, was of the order of 20 nm. Converting this to a weight of avidin, and assuming that the molecular weight of avidin is approximately 68,000, we obtain $1.4 \times 10^{-12}$ M×68,000=$9.5 \times 10^{-8}$ g (95 ng), which corresponds to an adsorption amount of 4.8 ng for a peak shift (wavelength shift) of 1 nm.

<Detection of Wavelength Change by Differential Spectrum Measurement and Operation of Electrical Circuit>

The spectrum (bold line in FIG. 19) of the interference light due to the optical interference unit and the spectrum (thin line in FIG. 19) of the interference light when the switching signal (avidin) was captured, were measured. This result is shown in FIG. 19. As is clear also from the spectral data of FIG. 19, the two spectral curves almost coincide with each other, and it is difficult to detect the wavelength shift of the interference light from this spectral curve data. However, if the differential spectrum of the two spectral data is taken using the spectrophotometer, the result is as shown in FIG. 20, and the wavelength difference of the two spectra which was very difficult to detect in FIG. 19, appears as a large wavelength difference. Therefore, by detecting the differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it can be detected with high sensitivity by amplification.

An arrangement was made in which the spectrophotometer activates a computer provided as a circuit operation controlling unit when it detects a differential spectrum so as to turn on a switch of an electric circuit and light up a lamp. The lamp was lit when the spectrophotometer detected a differential spectrum, confirming the operation of the circuit.

Next, in the optical interference unit an identical procedure was followed except that the silicon substrate was replaced by an interference filter and the film-like material was replaced by a laminate of 88 layers of the rod-shaped organic molecules 10.

Herein, the interference light spectrum due to the interference filter itself 101 (bold line in FIG. 21) and the interference light spectrum due to an interference filter provided with the film-like material 103 (thin line in FIG. 21), were measured. This result is shown in FIG. 21. As is clear from the spectral data of FIG. 21, the two spectral curves resemble each other, and it is difficult to detect the wavelength shift (peak shift) of the interference light from this spectral curve data. However, if the differential spectrum of the two spectral data is taken by the spectrophotometer, the result is as shown in FIG. 22, and the wavelength difference of the two spectra which was very difficult to detect in FIG. 21, now appears as a large wavelength difference. Therefore, by detecting the differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it can be detected with high sensitivity by amplification. Therefore, even if the silicon substrate is replaced by the interference filter, by measuring the differential spectrum in an identical way to the case where a silicon substrate is used, high sensitivity detection of the switching signal is possible, and switching of a circuit is possible.

Example 2

An oxide film ($SiO_2$ film) 50a was formed on the surface of a silicon substrate by heat-treating the silicon substrate (Shin-Etsu Chemicals) at approximately 1000° C. for 3 hours. For this pre-colored substrate, its interference light (peak top is about 508 nm (thin line in FIG. 18)) is green, and it had a green color. The surface area of the silicon substrate is $3 \times 10^{14}$ $nm^2$ (15 mm×20 mm).

On the other hand, according to the following synthesis scheme, poly benzyl-L-glutamate having biotin at the end ($PBLG_{21}$-bio) was synthesized as the α-helix polypeptide which is the rod-shaped organic molecule. Specifically, poly benzyl-L-glutamate ($PBLG_{21}$-bio) having a polymerization degree of 21 was synthesized by carrying out a polymerization of the benzyl-L-glutamate derivative (BLG-NCA) synthesized by the synthesis scheme shown in formula (3), using the biotin derivative shown in formula (4) as a polymerization initiator.

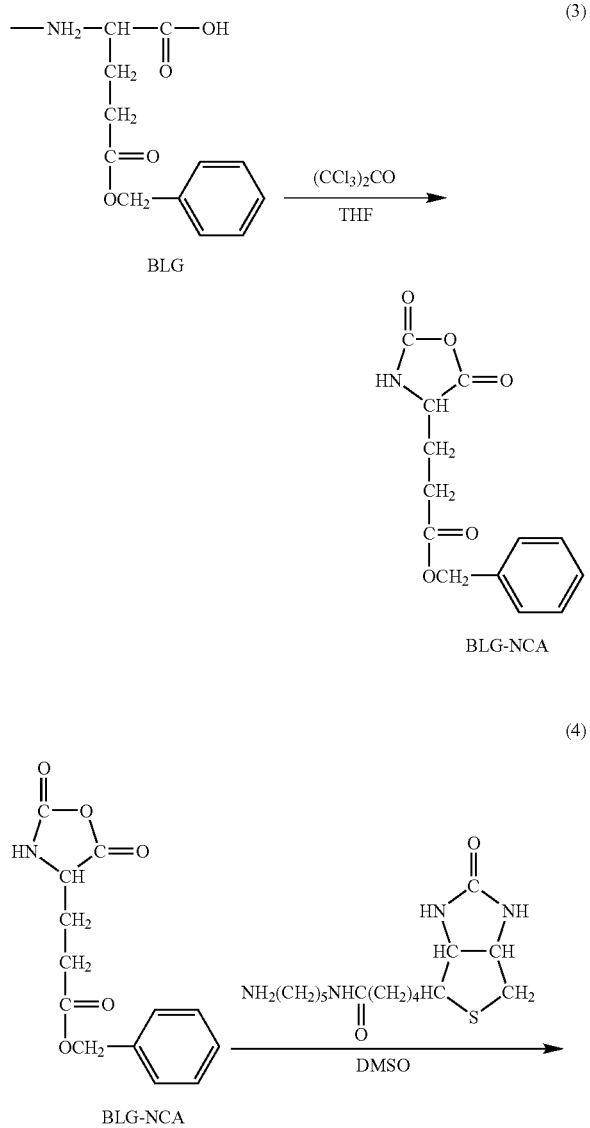

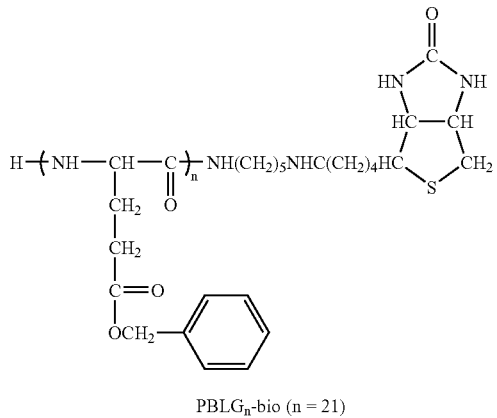

$PBLG_n$-bio (n = 21)

When the refractive index of this polybenzyl-L-glutamate ($PBLG_{21}$-bio) was measured using an Abbe's refractometer (Atago Co., Ltd.), it was about 1.5.

Ten layers of this synthetic polybenzyl-L-glutamate ($PBLG_{21}$-bio) were laminated on a substrate 50 by the LB method at a cumulative pressure of 9.5 mN/m (Shown in FIG. 9, laminated at a cumulative pressure on the vertical axis of 9.5 mN/m). Specifically, a lamination layer film 20 (film thickness approx. 13.25 nm) comprising ten layers of the monomolecular (film thickness approx. 1.33 nm) having this polybenzyl-L-glutamate ($PBLG_{21}$-bio) as the rod-shaped organic molecule 10, was formed (Shown in FIG. 10, where the lamination film does not show ten layers to simplify the illustration). The optical interference unit thus obtained gives an interference light color (interference color, peak top approx. 545 nm (dotted line of FIG. 18)) which is yellowish, and it had a yellowish color. The conditions under which this interference light is emphasized or enfeebled are as shown in the formulae of FIG. 11 wherein symbols and characters are as indicated in the upper drawing. FIG. 12A and FIG. 12B show the measurement of the interference light (interference color) in the pre-colored substrate (wherein the film-like material is not provided) (FIG. 12A), and the measurement of the interference light (interference color) in the optical interference unit (FIG. 12B).

Interaction Between Optical Interference Unit and Hazard Signal

The optical interference unit, i.e., the laminated film formed on the pre-colored substrate, was immersed in an aqueous solution ($1.1 \times 10^{-7}$ M) of avidin as the hazard signal, and biotin as the hazard signal capturing body in the optical interference unit was made to interact (adsorption reaction) with avidin which was the hazard signal. The cross-sectional surface area of avidin was a little less than about 30 $nm^2$ (3 nm×3 nm×3.14). FIG. 13 is a schematic diagram of the interaction (adsorption reaction) of biotin and avidin in this example, FIG. 14 is a schematic diagram showing the state where the optical interference unit is immersed in the aqueous solution of avidin, and FIG. 15 is a schematic diagram showing the interaction (adsorption reaction) of biotin in the optical detection unit with avidin in the aqueous solution of avidin. Subsequently, this optical detection unit was washed with pure water.

Wavelength Change Detection

As the optical irradiation unit, a spectrophotometer (Jasco Corp., V560) was used as a light source. Light (xenon lamp light) was irradiated by this optical irradiation unit so that the incidence angle on the optical interference unit was 10°. The reason why the incidence angle was selected to be 10°, was that the incidence angle was selected from measurement data of the incidence angle dependence of the interference light in FIGS. 16 and 17.

The spectrophotometer (Jasco Corp., V560) was disposed as a light-receiving unit in the path of the reflected light (interference light) due to the optical interference unit from the light irradiated by the optical irradiation unit to measure the spectral wavelengths of this reflected light (interference light), the peak top was 565 nm (bold line in FIG. 18), and a peak shift of approximately 20 nm was observed compared to the situation before the interaction between the optical interference unit and hazard signal. If calculations are performed assuming a refractive index of 1.5, this 20 nm corresponds to a film thickness variation of approximately 7.16 nm. This is confirmed to be due to adsorption of avidin having a diameter of approximately 6 nm on the surface of the optical interference unit.

<Calculation of Avidin Adsorption Amount>

The number of avidin adsorptions on the substrate can be computed from cross-sectional surface area of substrate/cross-sectional surface area of one avidin molecule, and was found to be $3 \times 10^{14}/3 \times 10^1 = 1 \times 10^{13}$ parts. Next, the number of absorption moles of avidin on this substrate can be computed from this number of adsorptions/Avogadro's number, and was found to be $1 \times 10^{13}/6 \times 10^{23} = 17 \times 10^{-12} M = 17$ pM.

Therefore, it was found that the avidin adsorption amount for a wavelength shift in the interference light of 20 nm is 17 pM.

Further, when the surface area of the substrate was approximately 5 mm$^2$, the wavelength shift (peak top shift) of the interference light for an avidin adsorption amount of 1.4 pM, was of the order of 20 nm. Converting this to a weight of avidin, and assuming that the molecular weight of avidin is approximately 68,000, we obtain $1.4 \times 10^{-12}$ M×68,000=$9.5 \times 10^{-8}$ g (95 ng), which corresponds to an adsorption amount of 4.8 ng for a peak shift (wavelength shift) of 1 nm.

<Detection of Wavelength Change by Differential Spectrum Measurement and Activation of Hazard Evasive Apparatus>

The spectrum (bold line in FIG. 19) of the interference light due to the optical interference unit and the spectrum (thin line in FIG. 19) of the interference light when the hazard signal (avidin) was captured, were measured. This result is shown in FIG. 19. As is clear also from the spectral data of FIG. 19, the two spectral curves almost coincide with each other, and it is difficult to detect the wavelength shift of the interference light from this spectral curve data. However, if the differential spectrum of the two spectral data is taken using the spectrophotometer, the result is as shown in FIG. 20, and the wavelength difference of the two spectra which was very difficult to detect in FIG. 19, appears as a large wavelength difference. Therefore, by detecting the differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it can be detected with high sensitivity by amplification.

A computer and a waste water port shutter provided as a hazard evasive apparatus activating unit were arranged so that they could be activated when a spectrophotometer detected a differential spectrum, and the waste water port shutter operated accordingly.

Next, in the optical interference unit an identical procedure was followed except that the silicon substrate was replaced by an interference filter and the film-like material was replaced by a laminate of 88 layers of the rod-shaped organic molecules 10.

Herein, the interference light spectrum due to the interference filter itself 101 (bold line in FIG. 21) and the interference light spectrum due to an interference filter provided with the film-like material 103 (thin line in FIG. 21), were measured. This result is shown in FIG. 21. As is clear from the spectral data of FIG. 21, the two spectral curves resemble each other, and it is difficult to detect the wavelength shift (peak shift) of the interference light from this spectral curve data. However, if the differential spectrum of the two spectral data is taken by the spectrophotometer, the result is as shown in FIG. 22, and the wavelength difference of the two spectra which was very difficult to detect in FIG. 21, now appears as a large wavelength difference. Therefore, by detecting the differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it can be detected with high sensitivity by amplification. Therefore, even if the silicon substrate is replaced by the interference filter, by measuring the differential spectrum in an identical way to the case where a silicon substrate is used, high sensitivity detection of the hazard signal is possible, and activation of a hazard evasive apparatus is possible.

According to the present invention, it is possible to provide optical switches which can control an operation of a circuit by detecting, as a switching signal, existence of a substance of various kinds such as pathogens, physiological substances, and toxic substances, and which can be applied to various safety apparatuses.

Also, according to the present invention, it is possible to provide safety apparatuses which are suitable for hospitals, laboratories, factories, plants, and the like, and which can avoid a hazard by activating a hazard evasive apparatus upon detecting, as a hazard signal, existence of a substance of various kinds such as pathogens, physiological substances, and toxic substances.

What is claimed is:

1. An optical switch comprising:

an optical irradiation unit which irradiates light;

an optical interference unit which can interact with a switching signal, which interferes with light irradiated from the optical irradiation unit and radiates it as interference light, and which can vary the wavelength of the interference light after interaction with the switching signal; and a switching unit which is provided in the path of the interference light, which detects the wavelength change of the interference light radiated by the optical interference unit, and which conducts one of activating and deactivating a circuit.

2. An optical switch according to claim 1, the optical interference unit comprising a film-like material.

3. An optical switch according to claim 2, the film-like material comprising a rod-shaped material.

4. An optical switch according to claim 3, wherein the rod-shaped material comprises a signal interaction part which can interact with a switching signal.

5. An optical switch according to claim 4, wherein the signal interaction part is a signal capturing body which can capture the switching signal.

6. An optical switch according to claim 5, wherein the signal capturing body is at least one of enzymes, coenzymes, enzyme substrates, enzyme inhibitors, clathrate compounds, metals, antibodies, antigens, proteins, microorganisms, viruses, cell debris, metabolic products, nucleic acids, hormones, hormone receptors, lectins, sugars, physiologically active materials and physiologically active material receptors.

7. An optical switch according to claim 6, wherein the clathrate compound is selected from a monomolecular host compound, a polymolecular host compound, a polymer host compound, and an inorganic host compound, wherein
the monomolecular host compound is selected from cyclodextrin, a crown compound, cyclophane, azacyclophane, calixarene, cyclotriveratrylene, spherand, cavitand and, cyclic oligopeptide;
the polymolecular host compound is selected from urea, thiourea, deoxycholic acid, perhydrotriphenylene, and tri-o-thymotide;
the polymer host compound is selected from cellulose, starch, chitin, chitosan, and polyvinyl alcohol; and
the inorganic host compound is selected from an interlayer compound, zeolite, and a Hofmann complex.

8. An optical switch according to claim 5, wherein the switching signal is avidin and wherein the signal capturing body is biotin.

9. An optical switch according to claim 4, wherein the signal interaction part interacts with the switching signal by one of physical adsorption and chemical adsorption.

10. An optical switch according to claim 3, wherein the rod-shaped material is a rod-shaped organic molecule.

11. An optical switch according to claim 10, wherein the rod-shaped organic molecule is a helical molecule.

12. An optical switch according to claim 11, wherein the helical molecule is an α-helix polypeptide.

13. An optical switch according to claim 2, further comprising a substrate on which the film-like material is disposed.

14. An optical switch according to claim 13, the substrate comprising a different refractive index film formed on a surface of the substrate, the different refractive index film having a refractive index different from a refractive index of the film-like material.

15. An optical switch according to claim 14, comprising a plurality of different refractive index films wherein refractive indices of the different refractive index films differ from each other.

16. An optical switch according to claim 14, wherein the different refractive index film is a dielectric film.

17. An optical switch according to claim 14, wherein the refractive index of the different refractive index film is different from a refractive index of the substrate.

18. An optical switch according to claim 13, the substrate comprising at least one of semiconductor, ceramics, metal, glass, and plastics.

19. An optical switch according to claim 13, the substrate comprising an identical refractive index film formed on a surface of the substrate, the identical refractive index film having the same refractive index as a refractive index of the film-like material.

20. An optical switch according to claim 13, wherein the substrate is an interference filter.

21. An optical switch according to claim 2, further comprising a film provided on a surface of the film-like material.

22. An optical switch according to claim 21, the film having the same refractive index as a refractive index of a surface of the substrate adjacent to the film-like material.

23. An optical switch according to claim 2, wherein a thickness of the film-like material is from 50 nm to 1 µm.

24. An optical switch according to claim 2, wherein the file-like material is one of monomolecular film of the rod-shaped material and a laminated film of the monomolecular films.

25. An optical switch according to claim 2, wherein the film-like material is formed by coating.

26. An optical switch according to claim 1, the switching unit comprising:
a wavelength change detecting part which is deposited in a path of the interference light and detects a wavelength change of the interference light radiated from the optical interference unit; and
a circuit controlling part which performs one of activating and deactivating a circuit when the wavelength change detecting part detects the wavelength change of the interference light.

27. An optical switch according to claim 26, wherein the wavelength change detecting part can measure a spectrum of interference light before a wavelength change, a spectrum of interference light after the wavelength change, and a differential spectrum of the two spectra.

28. An optical switch according to claim 27, wherein the wavelength change detecting part transforms the differential spectrum to spectral intensity and can amplify the spectral intensity.

29. An optical switch according to claim 27, wherein the wavelength change detecting part is a spectrophotometer.

30. An optical switch according to claim 26, wherein the wavelength change detecting part allows light having specific wavelengths to transmit therethrough and can detect transmittance of the light having specific wavelengths.

31. An optical switch according to claim 30, the wavelength change detecting part comprising:
an interference filter; and
an optical detection sensor which can detect light transmitted through the interference filter.

32. An optical switch according to claim 26, wherein the circuit activation controlling part is a computer.

33. An optical switch according to claim 1, wherein the optical interference unit irradiates interference light as at least one of reflected light and transmitted light.

34. An optical switch according to claim 1, wherein the optical irradiation unit can irradiate a light beam.

35. An optical switch according to claim 1, wherein the optical irradiation unit is a laser.

* * * * *